(12) United States Patent
Weng et al.

(10) Patent No.: US 7,897,113 B2
(45) Date of Patent: Mar. 1, 2011

(54) FLUIDIC DEVICES AND CONTROLLING METHODS THEREOF

(75) Inventors: Kuo-Yao Weng, Hsinchu (TW);
Nien-Jen Chou, Hsinchu (TW);
Chung-Hsien Tsai, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 380 days.

(21) Appl. No.: 12/054,392

(22) Filed: Mar. 25, 2008

(65) Prior Publication Data

US 2008/0171342 A1 Jul. 17, 2008

Related U.S. Application Data

(63) Continuation-in-part of application No. 11/612,869, filed on Dec. 19, 2006, and a continuation-in-part of application No. 11/612,882, filed on Dec. 19, 2006, now Pat. No. 7,794,665, and a continuation-in-part of application No. 11/612,896, filed on Dec. 19, 2006.

(60) Provisional application No. 60/831,285, filed on Jul. 17, 2006.

(30) Foreign Application Priority Data

Jul. 10, 2007 (TW) .............................. 96125027 A

(51) Int. Cl.
*G05D 9/00* (2006.01)
(52) U.S. Cl. ................... 422/106; 422/68.1; 435/287.1; 137/832; 137/833
(58) Field of Classification Search ........................ None
See application file for complete search history.

(56) References Cited

U.S. PATENT DOCUMENTS

| | | | |
|---|---|---|---|
| 5,065,768 A | | 11/1991 | Coleman et al. |
| 5,082,723 A | * | 1/1992 | Gross et al. .................. 442/118 |
| 6,408,884 B1 | | 6/2002 | Kamholz et al. |
| 6,415,821 B2 | | 7/2002 | Kamholz et al. |
| 6,521,188 B1 | | 2/2003 | Webster |
| 6,599,098 B2 | | 7/2003 | Weng et al. |
| 6,644,944 B2 | | 11/2003 | Karp |
| 6,756,018 B2 | | 6/2004 | Nishimura et al. |
| 6,766,817 B2 | | 7/2004 | da Silva |
| 6,782,746 B1 | | 8/2004 | Hasselbrink, Jr. et al. |
| 6,929,239 B1 | | 8/2005 | Colin et al. |
| 7,104,517 B1 | * | 9/2006 | Derand et al. .................. 251/11 |
| 7,419,821 B2 | * | 9/2008 | Davis et al. .............. 435/288.5 |

(Continued)

*Primary Examiner*—In Suk Bullock
*Assistant Examiner*—Timothy G Kingan
(74) *Attorney, Agent, or Firm*—Jianq Chyun IP Office

(57) ABSTRACT

A fluidic device for performing assays can include control components such as vacuum pumps, gas pumps, "broken open valves," and "self-close valves" for controlling the flow of fluids in the fluidic device. The vacuum pump can be used to pull a fluid in a specific direction in a channel, and the gas pump can be used to push a fluid in a specific direction in a channel. The broken open valve can be used to connect two separate regions at the control of a user, and the self-close valve can be used to automatically seal off a channel after passage of a fluid. The vacuum pumps, gas pumps, broken open valves, and self close valves can be made small in volume so that the fluidic device can be made as a small and portable device.

9 Claims, 34 Drawing Sheets

U.S. PATENT DOCUMENTS

| | | | |
|---|---|---|---|
| 2001/0044620 A1* | 11/2001 | Krulevitch et al. | 604/892.1 |
| 2002/0033193 A1* | 3/2002 | McNeely et al. | 137/825 |
| 2005/0239210 A1* | 10/2005 | Iida | 436/164 |
| 2006/0245933 A1 | 11/2006 | Balch et al. | |
| 2007/0150061 A1* | 6/2007 | Trieu | 623/17.12 |
| 2007/0164641 A1* | 7/2007 | Pelrine et al. | 310/800 |
| 2008/0003145 A1* | 1/2008 | Nurse et al. | 422/99 |

* cited by examiner

Materials

| Materials to be used | (° C.) | Sublimation Materials |
|---|---|---|
| Ammonium dicarbonate $(NH_4)CO_3$ | 60 | $NH_3CO_2$, $H_2O$ |
| Sodium dicarbonate $(NaHCO_3)$ | 100~140 | $CO_2$, $H_2O$ |
| Sodium borohydride $(NaBH_4)$ | 300 | $CO_2$, $H_2O$ |
| Azobisisobutyronitrile (AZDN) | 105 | $N_2$ |
| $(CH_3)_2(CN)C-N-NNNC(CN)(CH_3)_2$ N,N'dimethy-N,N' dinitroso-terephthalamide | 118 | $N_2$ |
| $(C_6H_4)-[Con(CH_3)-NO]_2$ 4,4'-Oxybis (bcnzenesulfonhydrazide) (OBSH) | 164 | $N_2$ |
| 3,3'-Sulfonbis(benzene-sulfonhydrazide)(D-33) | 148 | $N_2$ |
| $SO_2(C_6H_4SO_2NH-NH_2)_2$ N,N'-Dinitroso Pentantethylene tetramine (DPT) other organic foaming agents | 195 | $N_2$ |

FIG. 4B

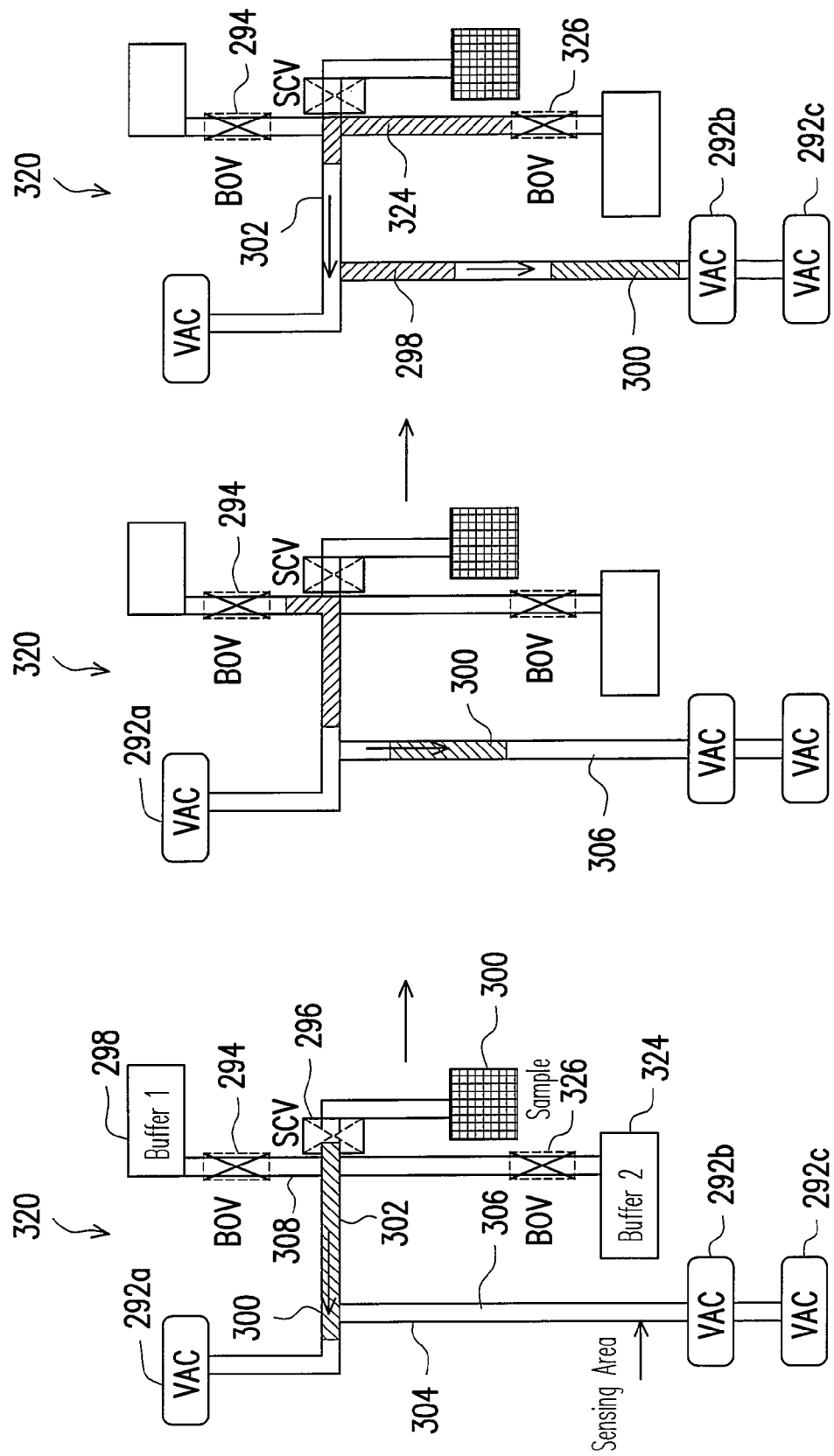

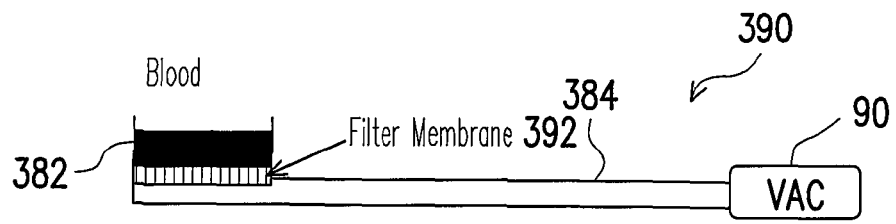
FIG. 23A
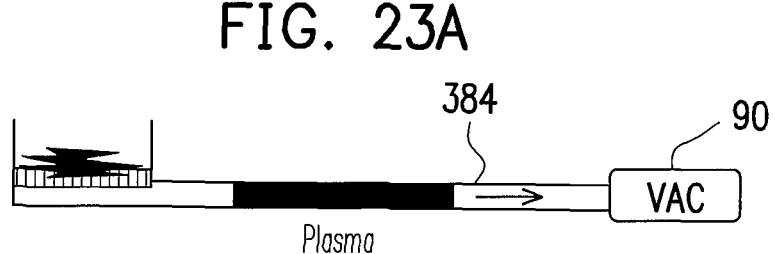
FIG. 23B
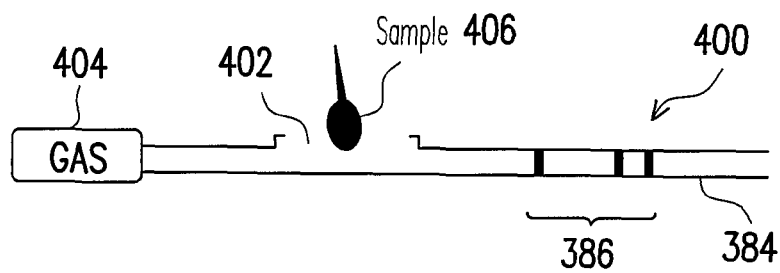
FIG. 24A
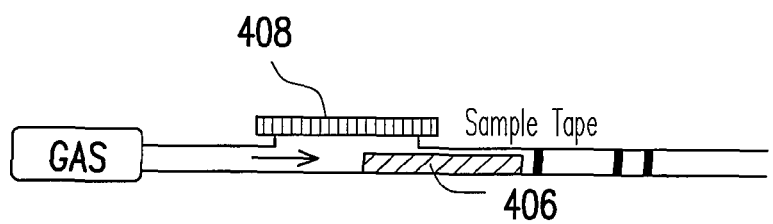
FIG. 24B
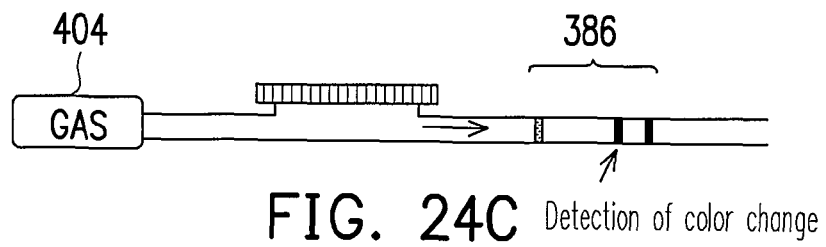
FIG. 24C   Detection of color change

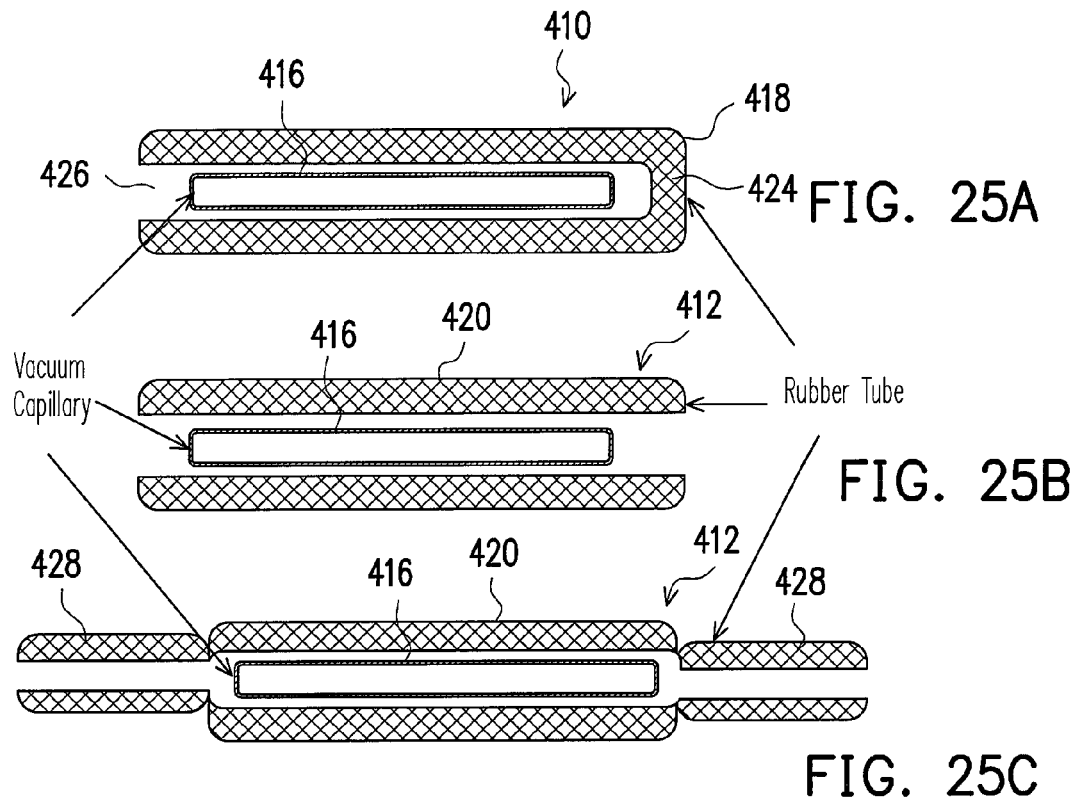
FIG. 25A
FIG. 25B
FIG. 25C
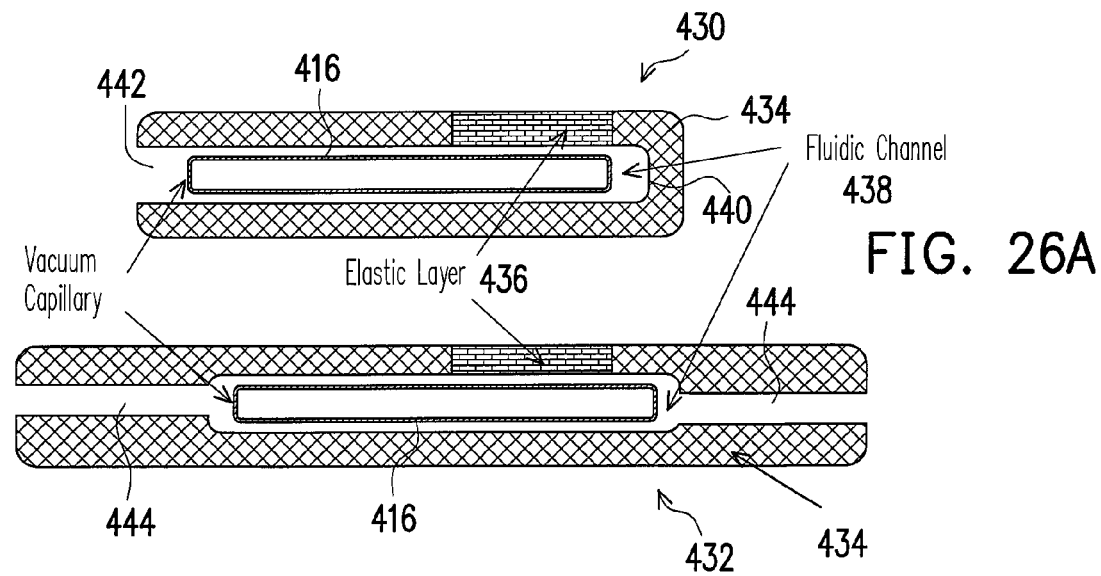
FIG. 26A
FIG. 26B

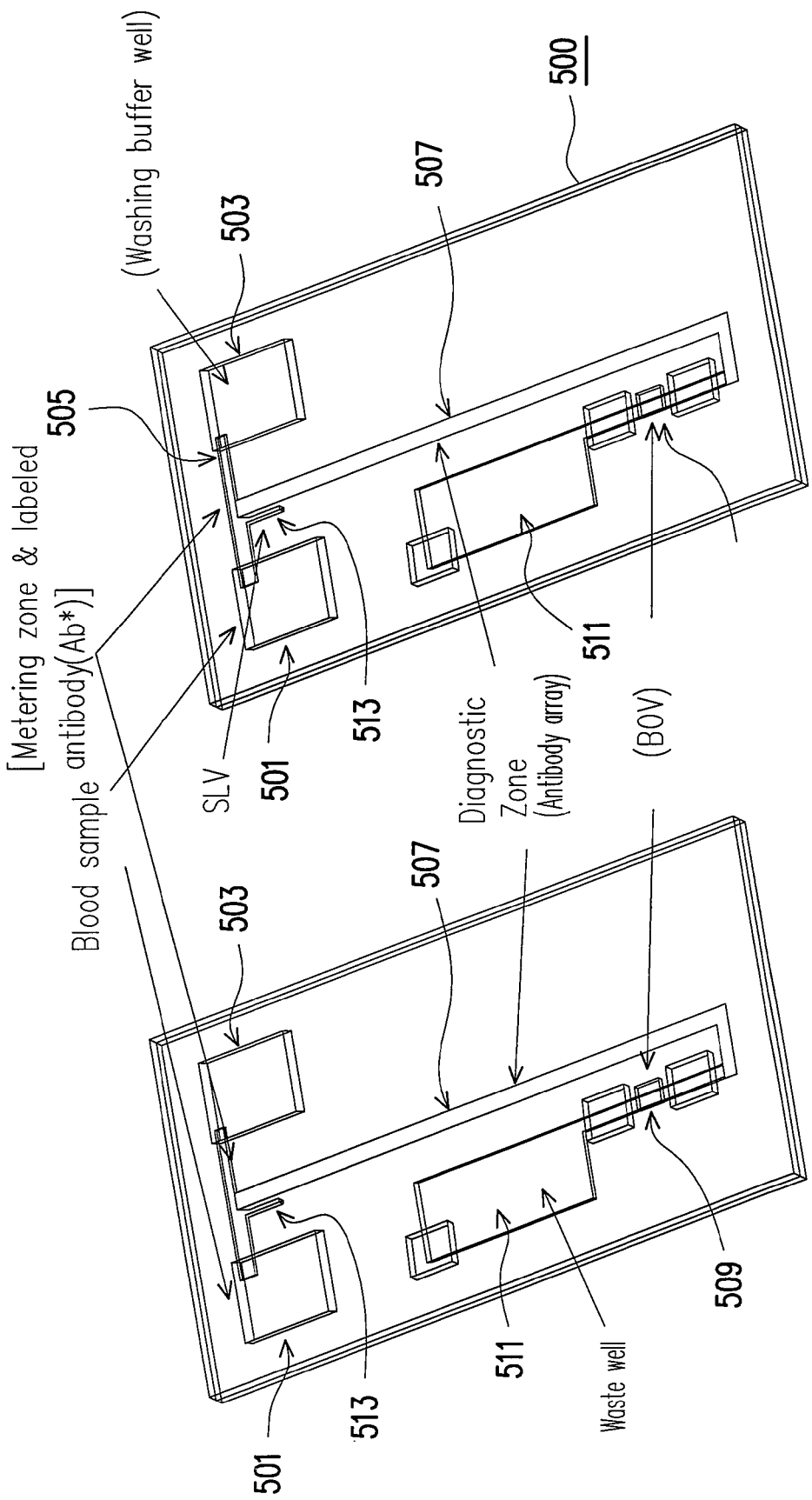

FLUIDIC DEVICES AND CONTROLLING METHODS THEREOF

CROSS-REFERENCE TO RELATED APPLICATION

This is a continuation-in-part application of patent application Ser. Nos. 11/612,869, 11/612,882, 11/612,896, all filed on Dec. 19, 2006, and all of which claim the benefit of U.S. Provisional Application No. 60/831,285, filed on Jul. 17, 2006. The application also claim the priority benefit of Taiwan patent application serial no. 96125027, filed on Jul. 10, 2007. The entirety of each of the above-mentioned patent applications is hereby incorporated by reference herein and made a part of this specification.

BACKGROUND OF THE INVENTION

1. Field of the Invention

The description relates to fluidic devices and controlling methods thereof.

2. Description of Related Art

Many types of testing devices can be used in detecting the presence of compounds or analyzing bio-chemical reactions. For example, lateral flow assays can be performed using a lateral flow membrane having one or more test lines along its length. A fluid with dissolved reagents travels from one end of the membrane to the test lines by electro osmosis. A reader detects whether reaction occurred at the test lines, which indicate the presence or absence of certain particles in the reagents. As another example, a device with an array of micro capillaries can be used to control the flow of fluids in immunoassay processes. Reagents are positioned at various locations along the lengths of the micro capillaries so that as fluids flow in the micro capillaries due to capillary force, the fluids come into contact with the reagents. A reader monitors the sites where the reagents are located to determine whether reactions have occurred. As yet another example, micro fluidic chips can be used to perform assays by controlling the flow of fluids through various channels and chambers. The micro fluidic chips are used with an external power supply and/or pump that provide the driving force for moving the fluids.

SUMMARY OF THE INVENTION

A fluidic device for performing assays can include control components such as vacuum pumps, gas pumps, "broken open valves," and "self-close valves" for controlling the flow of fluids in the fluidic device.

The vacuum pump can be used to pull a fluid in a specific direction in a channel, and the gas pump can be used to push a fluid in a specific direction in a channel.

The broken open valve can be used to connect two separate regions at the control of a user, and the self-close valve can be used to automatically seal off a channel after passage of a fluid.

The vacuum pumps, gas pumps, broken open valves, and self close valves can be made small so that the fluidic device can be made small and portable.

The present invention provides a method for controlling a flow of a fluid in a channel. The method comprises breaking a first container to generate a pressure difference in the channel so as to cause the fluid to move in the channel, and the first container is made of a brittle material. The first container (a) defines a space within the first container having a gas pressure that is different from the gas pressure outside of the first container, or (b) includes a first material that is separated from a second material prior to the breaking of the first container, the first and second materials selected to generate gas upon interaction of the first and second materials.

The present invention provides a fluidic device, including a channel and a first container. When the first container is broken, a pressure difference is generated in the channel. The first container is made of a brittle material. The first container (a) defines a space within the first container having a gas pressure that is different from the gas pressure outside of the first container, or (b) includes a first material that is separated from a second material prior to the breaking of the first container, the first and second materials are selected to generate gas upon interaction of the first and second materials.

The present invention provides a fluidic device, which comprises a first material defining a first region and a second material defining a second region that is separated from the first region. The fluidic device further comprises a connector coupled between the first region and the second region, and the connector comprises a brittle material and has an open end and a closed end. The open end is disposed in the second region and the closed end is disposed in the first region. The first region is closed off from the second region by the closed end of the connector. The connector is configured so that when the closed end of the connector is broken, the connector defines a passage from the first region to the second region.

The present invention provides a fluidic device, which comprises a channel having an expanded section with a diameter larger than that of adjacent portions of the channel, and the fluidic device further comprises a material disposed in the expanded section. The material has a volume that does not block a passage of a fluid prior to absorption of the fluid. Wherein, the material expands in volume upon absorption of a portion of the fluid so that, after expansion, the material blocks passage of additional fluid through the channel. The material comprises superabsorbent polymers.

The present invention provides a fluidic device, which comprises a first reservoir containing a first fluid, a second reservoir containing a second fluid, a main channel, a first branch channel, a second branch channel, a first one-use pump, and a second one-use pump. The first branch channel couples the first reservoir to the main channel. The second branch channel couples the second reservoir to the main channel. The first one-use pump generates a pressure difference to move one or both of the first and second fluids when a container in the first one-use pump is broken. The second one-use pump generates a pressure difference to move one or both of the first and second fluids when a container in the second one-use pump is broken.

The present invention provides a method for controlling a fluid, which comprises providing a plurality of pipettes to enable sampling of predetermined amounts of fluids. Each pipette comprises a channel and a container which generates a pressure difference in the channel when the container is broken, the container being made of a brittle material. The container defines a space within the container having a gas pressure that is less than the gas pressure outside of the container, wherein breaking the container generates a predetermined amount of pressure difference in the channel to cause a predetermined amount of fluid to be drawn into the channel.

The present invention provides a method for controlling a fluid, which comprises enabling a fluid to flow from a first region to a second region, wherein the first region is coupled to the second region by a connector having an open end and a closed end. The open end is disposed in the second region and the closed end is disposed in the first region. The first region is closed off from the second region by the closed end of the connector, wherein enabling the fluid to flow comprises breaking the closed end of the connector to form a passage from the first region to the second region through the connector. A material, which absorbs a fluid and expands in volume, is used to absorb a portion of the fluid flowing through the connector, and the expanded material is used to block further flow of additional fluid through the connector.

The present invention provides a method for controlling a fluid, which comprises flowing a fluid in a channel that includes a material which expands in volume upon absorption of a portion of the fluid. Flowing the fluid in the channel includes flowing a first portion of the fluid past the material and using the material to absorb a second portion of the fluid to cause the material to expand in volume. The expanded material is used to block a passage of additional fluid through the channel.

The present invention provides a method for controlling a fluid, which comprises passing a fluid through a channel that includes a first self-close valve and a second self-close valve. The first and second self-close valves spaced apart from each other, and each self-close valve comprises a fluid absorbing material that expands in volume upon absorption of a portion of the fluid. The fluid absorbing materials in the first and second self-close valves are used to absorb a portion of the fluid. The volume of the fluid absorbing materials is expanded to block further passage of additional fluid through the channel and to retain a predetermined amount of fluid in a section of the channel between the first and second self-close valves.

The present invention provides a method for controlling a fluid, which comprises breaking a first container made of a brittle material to generate a pressure difference in a channel so as to cause a first fluid to move from a first reservoir to a first segment of the channel. The first container (a) defines a space within the first container having a gas pressure that is different from the gas pressure outside of the first container, or (b) includes a first material that is separated from a second material prior to the breaking of the first container. The first and second materials selected to generate gas upon interaction of the first and second materials. A second container made of a brittle material is broken to generate a pressure difference in the channel so as to cause at least a portion of the first fluid to move through a second segment of the channel.

The present invention provides a method for controlling a fluid, which comprises simultaneously operating a first one-use pump and a second one-use pump to draw a first portion of a sample fluid to a first channel and a second portion of the sample fluid to a second channel. A first container in the first one-use pump is broken to generate a pressure difference so as to cause the first portion of the sample fluid to move from a reservoir to the first channel, and a second container in the second one-use pump is broken to generate a pressure difference so as to cause the second portion of the sample fluid to move from the reservoir to the second channel. A third one-use pump and a fourth one-use pump are simultaneously operated to draw a first buffer solution to the first channel and a second buffer solution to the second channel.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 4B is a table of materials.

FIGS. 19A to 19C are schematic diagrams of a device for use in a three-step assay.

FIGS. 23A and 23B are schematic diagrams of a device for sampling a filtered fluid.

FIGS. 24A to 24C are schematic diagrams of a device for performing a slow calorimetric assay.

FIGS. 25A and 25C are schematic diagrams of vacuum pumps.

FIGS. 26A and 26B are schematic diagrams of vacuum pumps.

FIGS. 29A and 29B show a device in an embodiment of the present invention, which is manufactured by a combination of a self-close valve (SLV) and a broken open valve (BOV) to perform an antibody assay on a blood sample.

DESCRIPTION OF EMBODIMENTS

A fluidic device for performing assays includes control components such as vacuum pumps, gas pumps, "broken open valves," and "self-close valves" for controlling the flow of fluids in the fluidic device. The vacuum pump can be used to pull a fluid in a specific direction in a channel, and the gas pump can be used to push a fluid in a specific direction in a channel. The broken open valve can be used to connect two separate regions at the control of a user, and the self-close valve can be used to automatically seal off a channel after passage of a fluid. The vacuum pumps, gas pumps, broken open valves, and self close valves can be made small so that the fluidic device can be made small and portable.

In the following description, the individual control components will be introduced first, followed by a description of how the control components can be combined to construct modular units for controlling fluids in fluidic devices. Afterwards, how biological assays can be performed using the fluidic devices will be described.

Figure 1A:
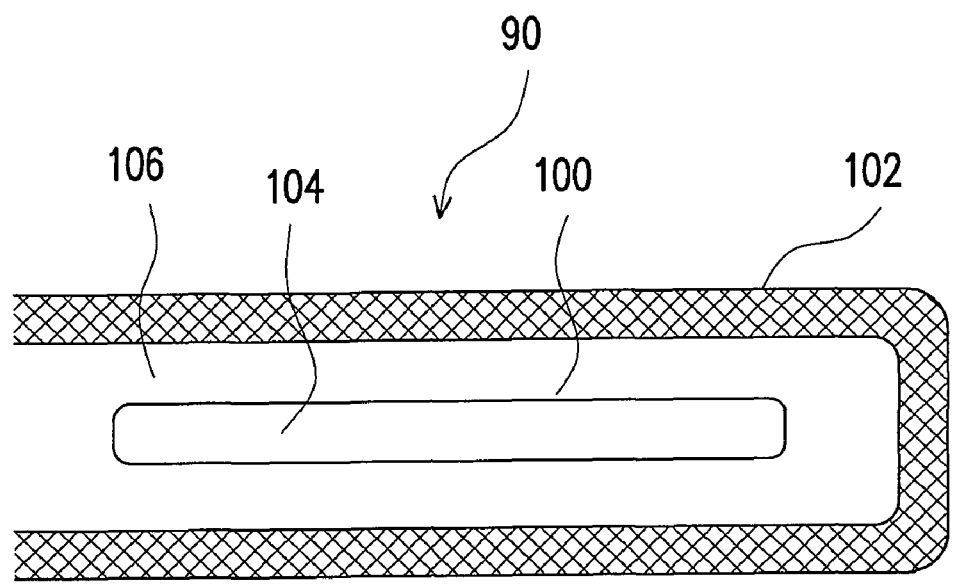
FIGS. 1A and 1B are schematic diagrams of a vacuum pump.

Referring to FIG. 1A, a vacuum pump 90 can be constructed by placing a container 100 in a channel 106 (or chamber) defined by a material 102. The container 100 encloses a region 104 that is vacuum or has a low gas pressure as compared to the gas pressure in the channel 106.

Figure 1B:
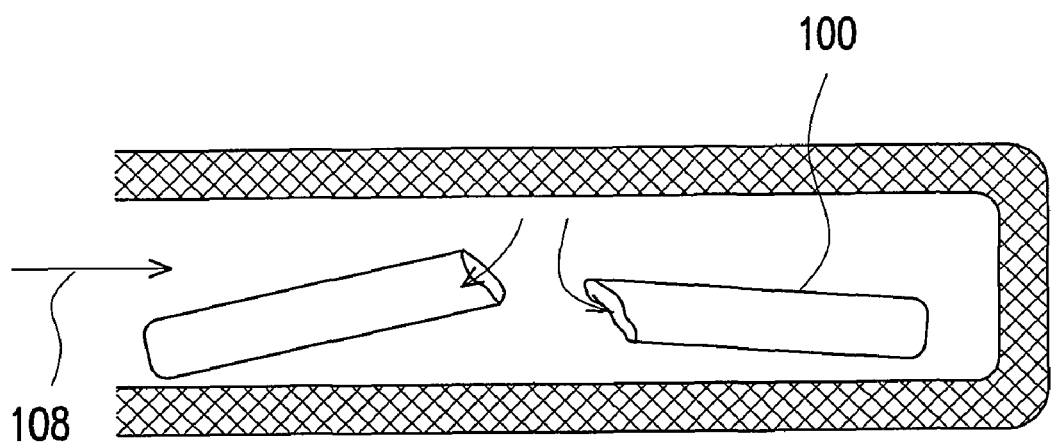

Referring to FIG. 1B, the container 100 can be, e.g., a glass capillary, that breaks upon application of an external force. When the container 100 breaks, gas in the channel 106 flows into the vacuum region 104, reducing the pressure in the region 106. This produces a suction force that can be used to pull a fluid in a direction 108 towards the region 106.

FIGS. 25A to 25C show examples of vacuum pumps using glass capillaries placed in rubber tubes. FIG. 25A shows a cross section of a gas pump 410 having a vacuum glass capillary 416 placed in a rubber tube 418, where the tube 418 has a closed end 424 and an open end 426. FIG. 25B shows a cross section of a gas pump 412 that is similar to the gas pump 410 except that the gas pump 412 has a rubber tube 420 with two open ends. FIG. 25C shows the gas pump 412 connected to two rubber tubes 428, where the rubber tube 420 has a larger inner diameter (to accommodate the glass capillary 416) than the rubber tubes 428.

FIGS. 26A and 26B show examples of vacuum pumps using glass capillaries placed in planar fluidic channels. FIG. 26A shows a cross section of a vacuum pump 430 having a vacuum glass capillary 416 placed in a fluidic channel 438 defined by a planar substrate 434. The fluidic channel 438 has a closed end 440 and an open end 442. The planar substrate 434 may be made of a rigid material. An elastic layer 436 is embedded in the substrate 434 at a location adjacent to the capillary 416 to allow a user to apply an external force through the elastic layer to break the capillary 416.

FIG. 26B shows a cross section of a vacuum pump 432 that is similar to the vacuum pump 430 except that the fluidic channel 438 is connected to two fluidic channels 444 having smaller cross sections.

A vacuum glass capillary can be made by heating one end of a glass capillary to melt the glass to form a first closed end. A vacuum pump is used to pump air out of the glass capillary through the open end. The glass capillary is heated at a location at a distance from the first closed end. The heat softens the glass, which can be pinched or twisted to form a second closed end.

Figure 2A:
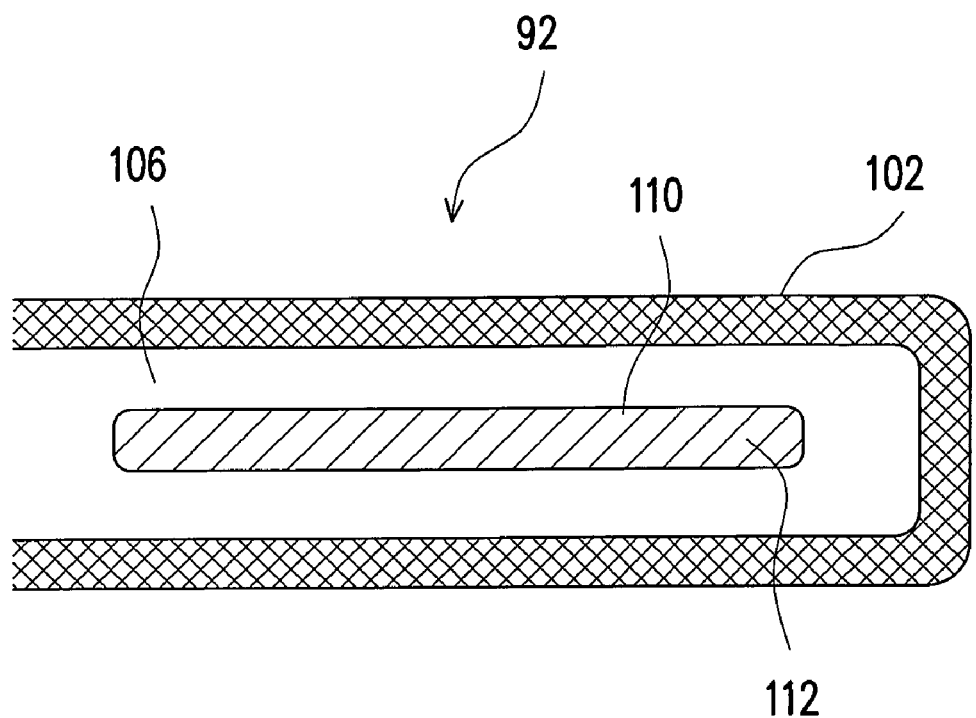
FIGS. 2A and 2B are schematic diagrams of a gas pump.

Referring to FIG. 2A, a gas pump 92 can be constructed by placing a container 110 in a channel 106 (or chamber) defined by a material 102. The container 110 encloses a region 112 that has a higher gas pressure compared to the gas pressure in the channel 106 outside of the container 110.

Figure 2B:
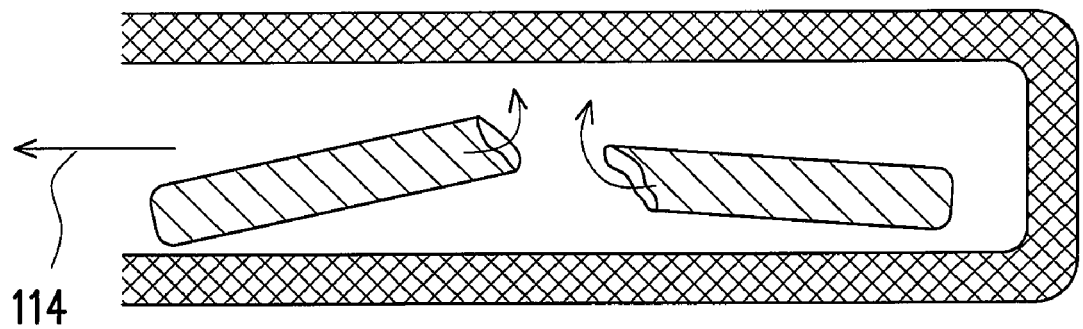

Referring to FIG. 2B, the container 110 can be, e.g., a glass capillary, that breaks upon application of an external force. When the container 110 breaks, gas originally inside the container 110 flows out of the container 110, increasing the pressure in the region 106. This produces a force that can be used to push a fluid in a direction 114 away from the region 106.

In this description, the term "vacuum pump" will be used to refer generally to a device that generates a pull force that can be used to pull a fluid towards the device, and the term "gas pump" will be used to refer generally to a device that generates a push force that can be used to push a fluid away from the device.

Figure 3A:
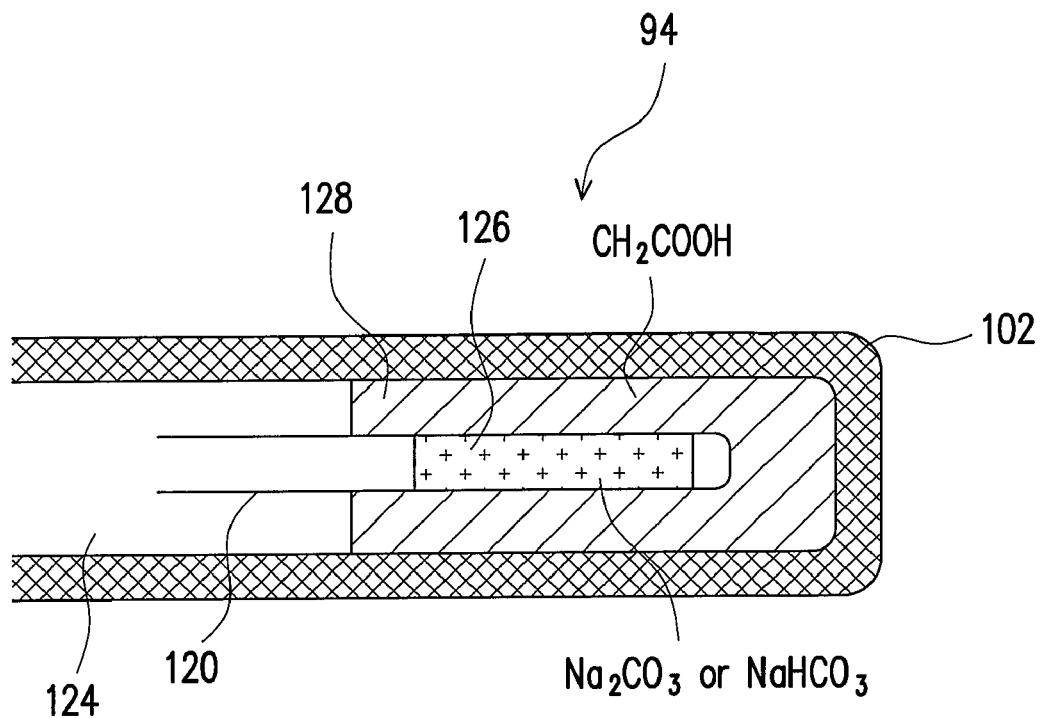
FIGS. 3A and 3B are schematic diagrams of a gas pump.

There are alternative ways to construct a gas pump. For example, referring to FIG. 3A, a gas pump 94 can be fabricated by placing a glass capillary 120 that is partially filled with a first material 126 in a channel 124 (or chamber) that contains a second material 128. The first and second materials 126 and 128 are selected so that when they intermix, the materials 126 and 128 will interact and generate one or more gases. For example, the first material 126 can be disodium carbonate ($Na_2CO_3$) and/or sodium hydrogen carbonate ($NaHCO_3$), and the second material 128 can be ethanoic acid ($CH_2COOH$).

Figure 3B:
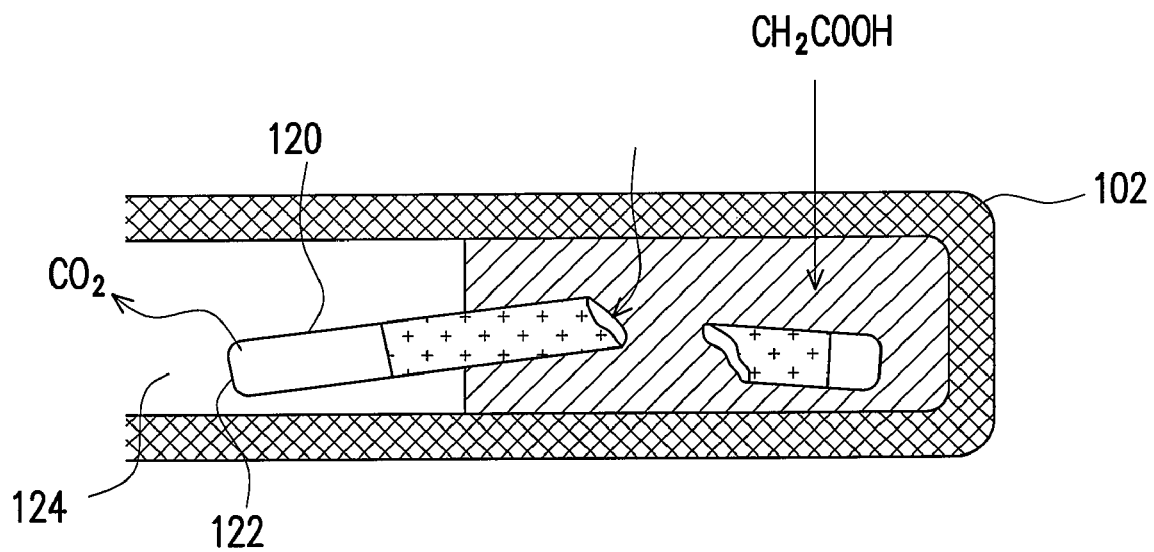

Referring to FIG. 3B, when an external force is applied to break the glass capillary 120, the first and second materials 126 and 128 interact and generate a gas. In this example, the gas is carbon dioxide ($CO_2$). The chemical reactions that occur are:

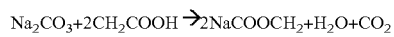

$$Na_2CO_3 + 2CH_2COOH \rightarrow 2NaCOOCH_2 + H_2O + CO_2$$

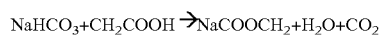

$$NaHCO_3 + CH_2COOH \rightarrow NaCOOCH_2 + H_2O + CO_2$$

The carbon dioxide increases the pressure in the channel 124, generating a force that can be used to push a fluid away from the broken capillary 120.

Figure 27A:
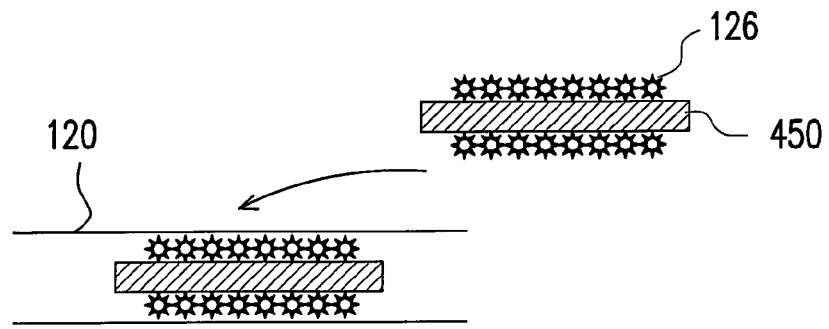
FIGS. 27A to 27C are schematic diagrams of self-close valves.
Figure 27B:
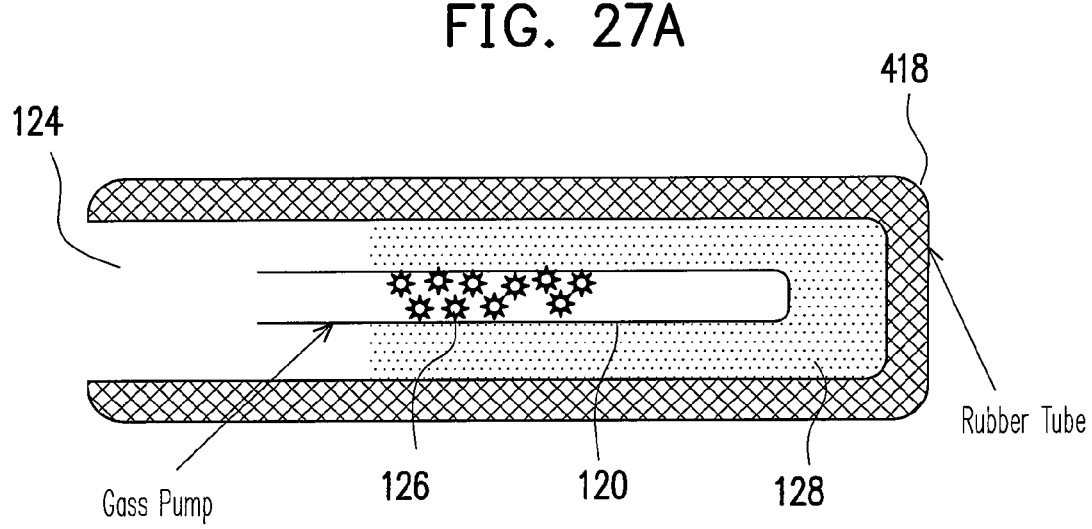
Figure 27C:
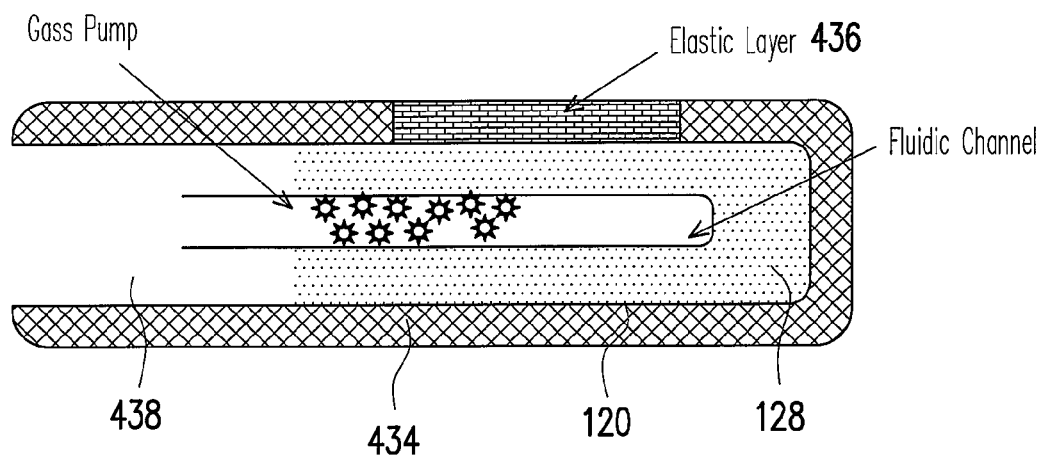

The first material 126 can be filled directly into the capillary 120. Referring to FIG. 27A, the first material 126 can also be attached to a wire 450, then the wire 450 along with the coated material 126 is placed inside the capillary 120. FIG. 27B shows an example in which the glass capillary 120 is placed in a channel 124 within a rubber tube 418. The channel 124 contains a second material 128 that can interact with the first material 126 when the glass capillary 120 is broken. FIG. 27C shows an example in which the glass capillary 120 is placed in a fluidic channel 438 within a planar device substrate 434. An elastic layer 436 is embedded in the substrate 434 at a location adjacent to the capillary 120 to allow a user to apply an external force through the elastic layer 436 to break the capillary 120.

Figure 4A:
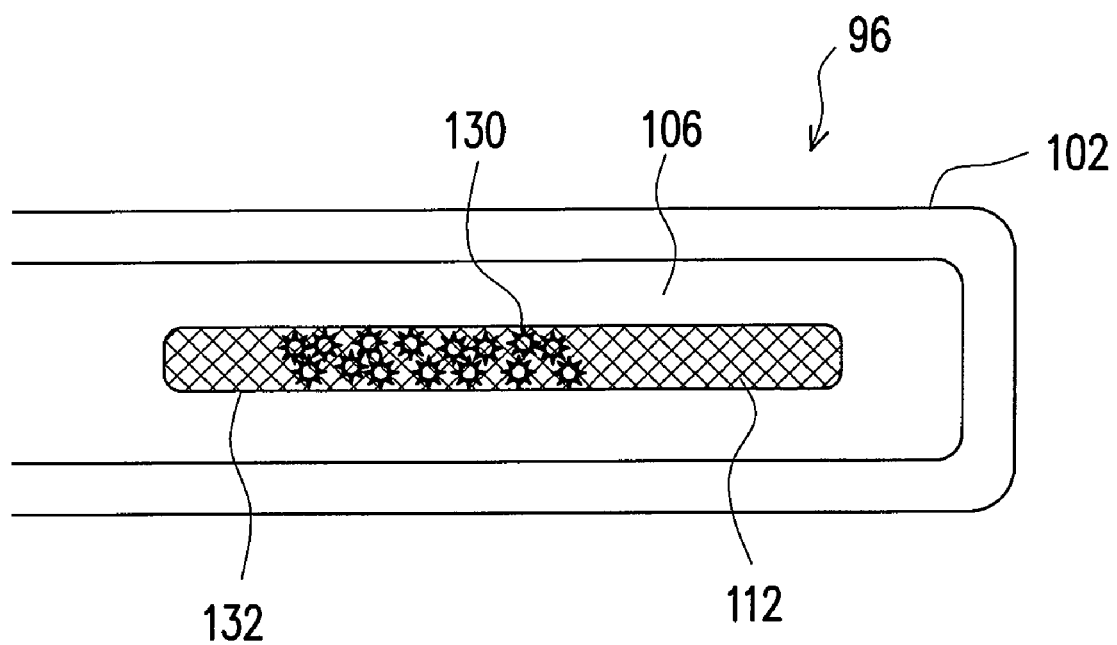
FIG. 4A is a schematic diagram of a gas pump.

Referring to FIG. 4A, a gas pump 96 can be fabricated by placing a compound 130 in a glass capillary 132, sealing the capillary 132, heating the capillary 132, cooling the capillary 132, and placing the capillary 132 in a channel 106 (or chamber). The compound 130 is selected to be a material that generates a gas after being heated. When the capillary 132 is heated and cooled, the gas generated from the compound 130 increase the gas pressure inside the capillary 132, as compared to the gas pressure outside of the capillary 132.

Examples of the compound 130 include sodium dicarbonate ($NaHCO_3$) and calcium carbonate ($CaCO_3$). These compounds generate carbon dioxide when heated:

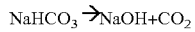

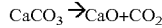

Sublimation materials that change from solid form to gas form (e.g. dry ice that turns into $CO_2$) can also be used. Other materials that generate gas when heated, such as $NaN_3$ generating nitrogen when heated ($2 NaN_3 \rightarrow 2Na+3N_2$), are listed in Table 1 of FIG. 4B.

Figure 5A:
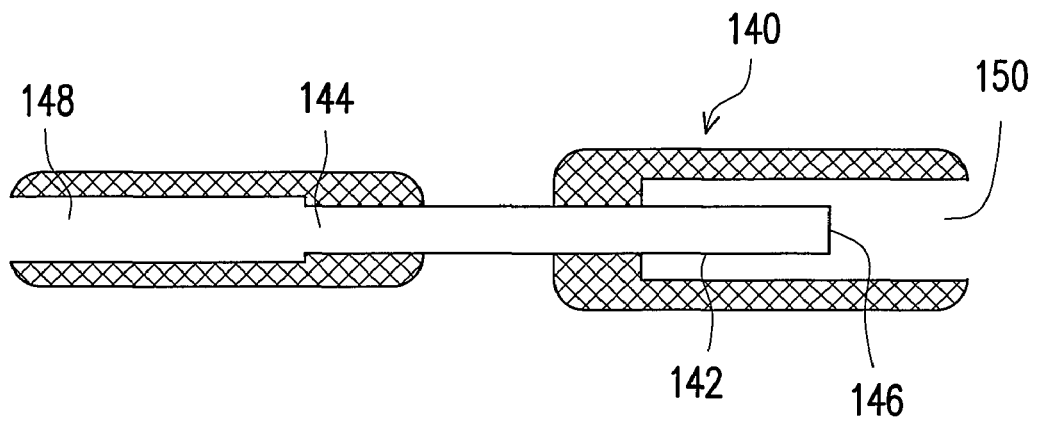
FIGS. 5A and 5B are schematic diagrams of a broken-open valve.

Referring to FIG. 5A, a broken open valve 140 can be fabricated by placing a glass capillary 142 between a first channel 148 and a second channel 150. The glass capillary 142 has an open end 144 that is positioned in the first channel 148, and a closed end 146 that is positioned in the second channel 150. When the glass capillary is intact, fluids cannot flow between the first and second channels 148 and 150. This is referred to as the "closed" state of the broken open valve 140.

Figure 5B:
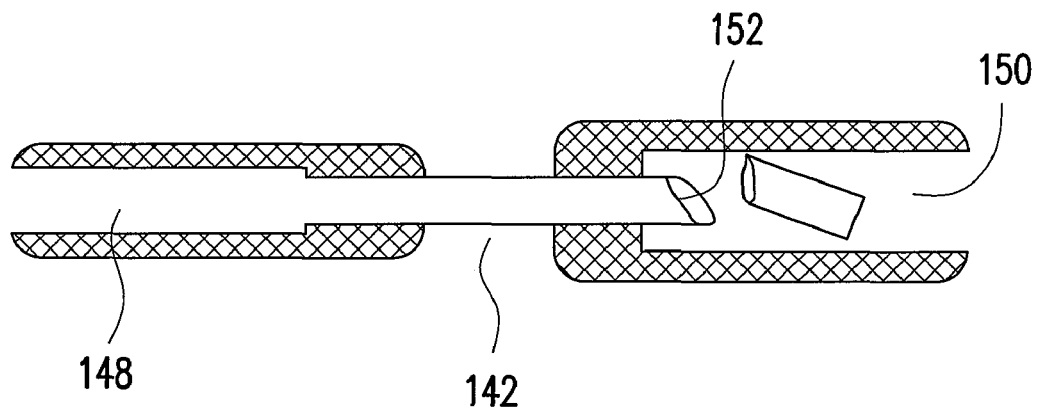

Referring to FIG. 5B, when an external force is applied to break the glass capillary 142, a passage 152 is formed that connects the channels 148 and 150. This is referred to as the "open" state of the broken open valve. The broken open valve 140 is useful in allowing two fluids (or a fluid and a solid) to be separated initially, then interact at a time controlled by the user.

Figure 28A:
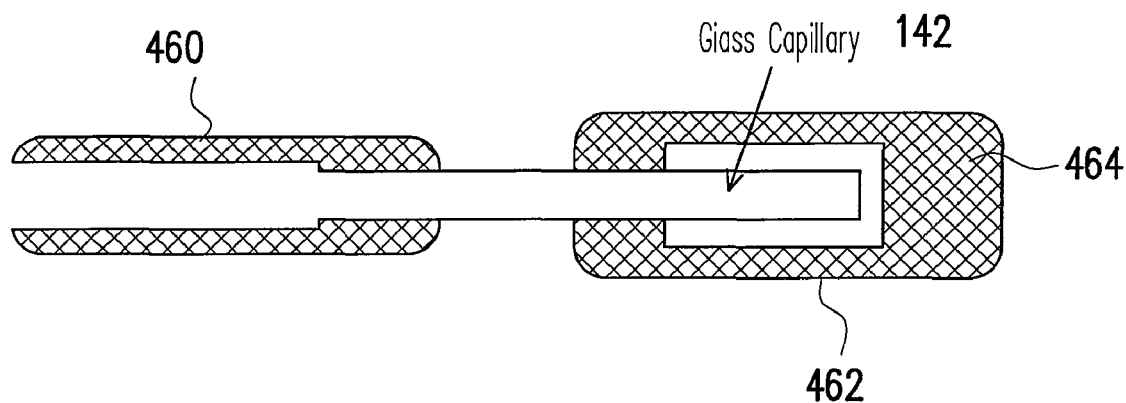
FIGS. 28A and 28B are schematic diagrams of a broken-open valve.
Figure 28B:
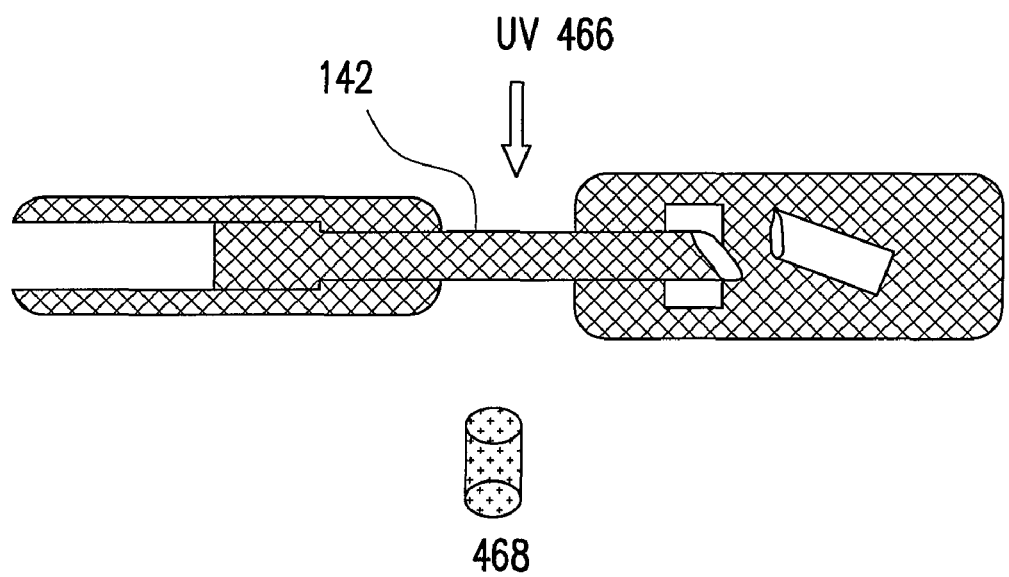

FIGS. 28A and 28B shows an example of using a broken-open valve to construct a low cost device for performing an assay in which a fluid is irradiated with ultra-violet (UV) light. A glass capillary 142 connects two plastic channels 460 and 462. Initially, a reactant 464 is contained in the first plastic channel 462. Upon breaking the glass capillary 142, the reactant 464 flows through the glass capillary 142 to the second plastic channel 460. As shown in FIG. 28B, a UV light source 466 irradiates the reactant 464 as it flows through the glass capillary 142. A detector 468 detects the UV light that passes the reactant 464. The spectrum of the UV light detected by the detector 468 is useful in determining the compounds in the reactant 464.

Figure 28C:
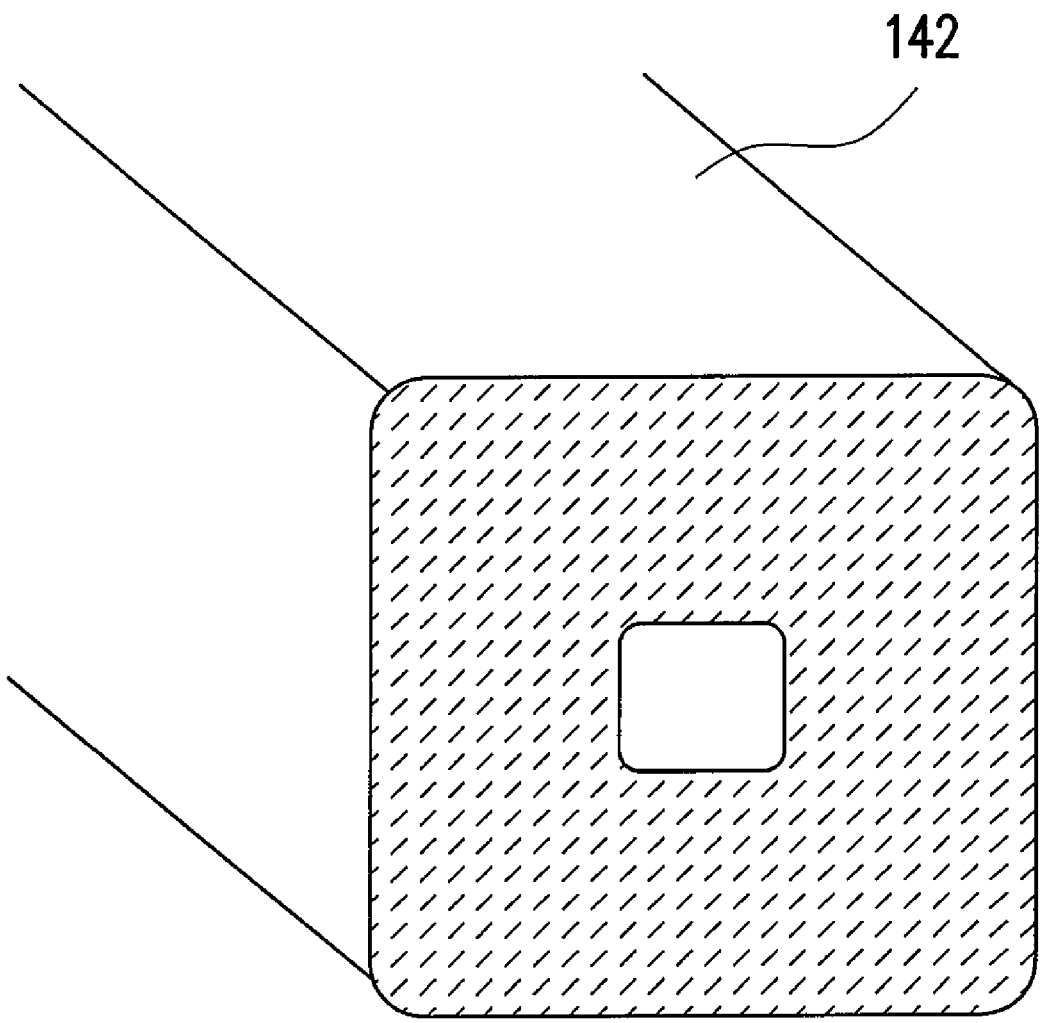
FIG. 28C is a cross-sectional view of a glass capillary having a square inner rim and a square outer rim.

FIG. 28C shows a cross section of a glass capillary having square shaped inner and outer perimeters. The square shaped inner and outer perimeters allow the UV light to pass the glass capillary in a direction that is perpendicular to the surface of the glass capillary. This allows more UV light to reach the fluid in the glass capillary, as compared to a capillary having a circular cross section that may cause the incident UV light to be reflected or redirected in directions away from the fluid.

Figure 6A:
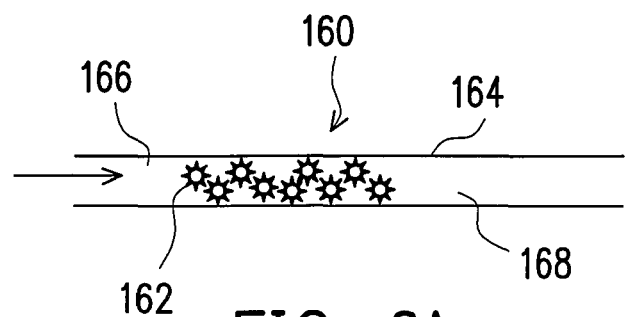
FIGS. 6A, 6B, 7A, 7B, and 8A to 8C are schematic diagrams of self-close valves.
Figure 6B:
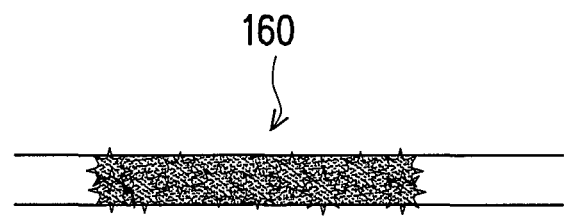

Referring to FIGS. 6A and 6B, a self-close valve 160 can be constructed by placing superabsorbent polymers (SAP) 162 in a channel 164. Initially, the SAP 162 has a smaller volume and allows fluids to flow between a first region 166 and a second region 168 in the channel 164 (FIG. 6A). This is referred to as the "open" state of the self-close valve. When a fluid flows past the SAP 162, the SAP absorb a portion of the fluid and expands in volume, blocking the channel 164 (FIG. 6B), preventing further fluid from flowing between the first region 166 and the second region 168. This is referred to as the "closed" state of the self-close valve.

Superabsorbent polymers can absorb and retain large volumes of water or other aqueous solutions. In some examples, SAP can be made from chemically modified starch and cellulose and other polymers, such as poly(vinyl alcohol) PVA, poly(ethylene oxide) PEO, which are hydrophilic and have a high affinity for water. In some examples, superabsorbent polymers can be made of partially neutralized, lightly cross-linked poly (acrylic acid), which has a good performance versus cost ratio. The polymers can be manufactured at low solids levels, then dried and milled into granular white solids. In water, the white solids swell to a rubbery gel that in some cases can include water up to 99% by weight.

Figure 7A:
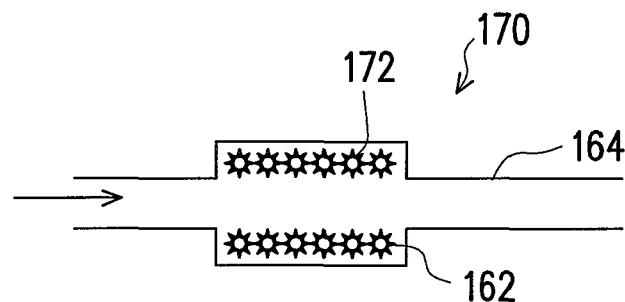

Referring to FIG. 7A, a self-close valve 170 can include a channel 164 that has an enlarged portion 172 to accommodate the superabsorbent polymers 162 so that the superabsorbent polymers 162 do not restrict flow of fluid before expansion of the SAP 162. To fabricate the self-close valve 170, an adhesive can be applied to the inner walls of the enlarged portion 172, the SAP 162 in powder form is then pushed into the channel 164 so that the SAP 162 powder adheres to the inner wall at the enlarged portion 172.

Figure 7B:
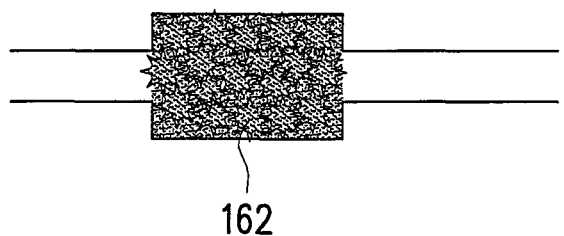

Referring to FIG. 7B, as the fluid flows past the superabsorbent polymers 162, the superabsorbent polymers 162 absorb a portion of the fluid and expands in volume, blocking the channel 164, preventing further flow of the fluid past the expanded polymers 162.

Figure 8A:
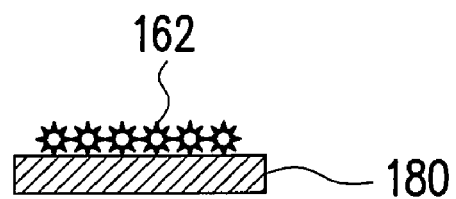
Figure 8B:
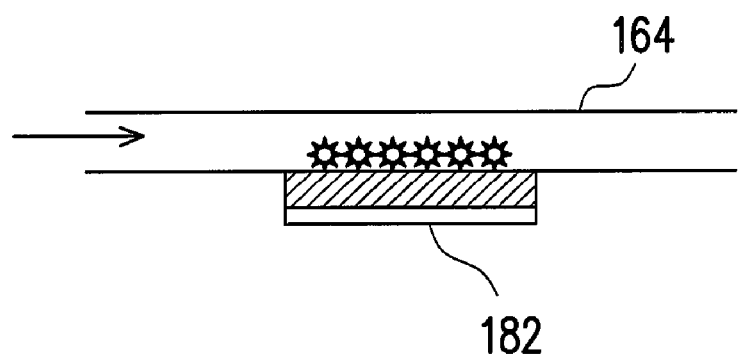

Referring to FIGS. 8A and 8B, superabsorbent polymers 162 can be attached to a wire 180, then placed into a channel 164. The channel 164 can have a recessed region 182 in which an adhesive is applied to secure the wire 180 at a predefined location.

Figure 8C:
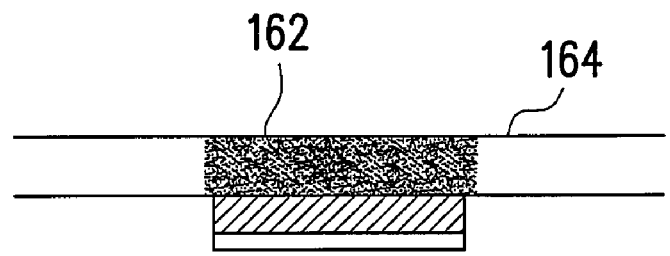

Referring to FIG. 8C, as the fluid flows past the superabsorbent polymers 162, the polymers 162 absorb a portion of the fluid and expands in volume, blocking the channel 164, preventing further flow of the fluid past the expanded polymers 162.

A self-close valve can be constructed by coating a wire with SAP, then placing the coated wire into a channel or tube. A self-close valve for use in a planar fluidic device can be constructed by coating a planar substrate with SAP, then placing the coated substrate into a planar channel in the planar fluidic device.

Figure 9A:
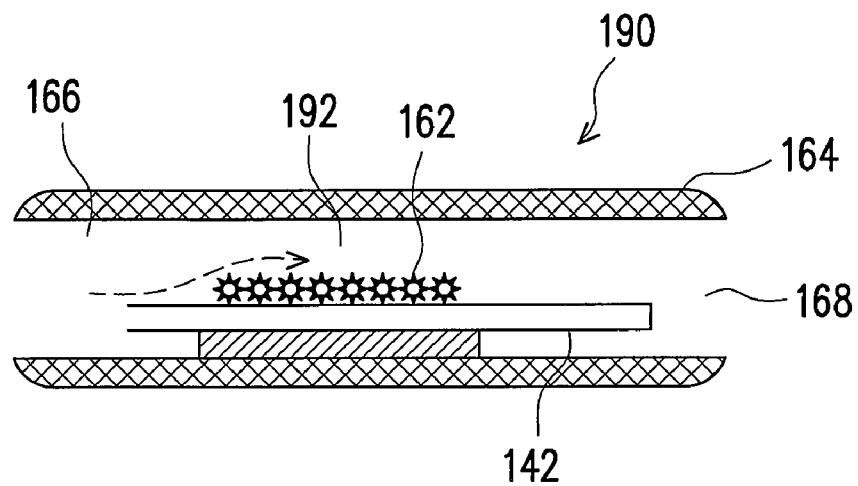
FIGS. 9A to 9C are schematic diagrams of an on-off-on valve.
Figure 9B:
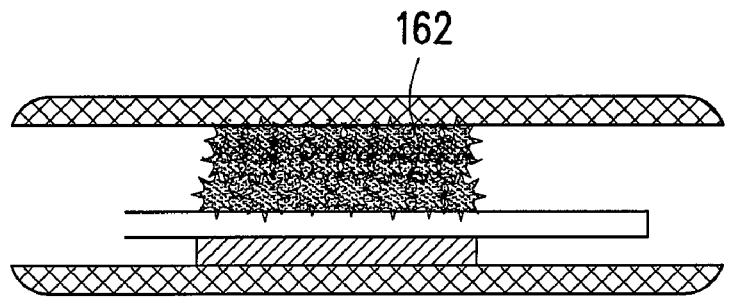
Figure 9C:
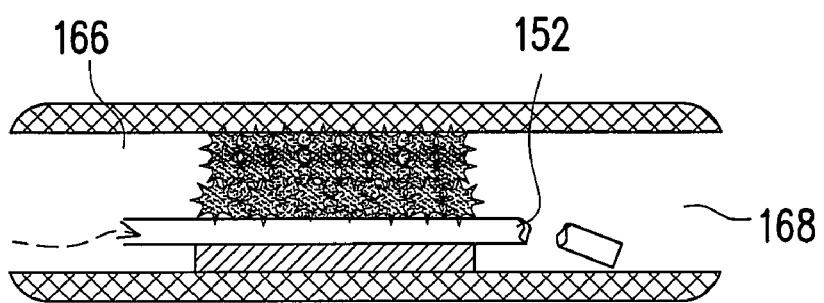

Referring to FIGS. 9A to 9C, an on-off-on valve 190 can be fabricated by using a glass capillary 142 and SAP 162 that are positioned outside of and adjacent to the capillary 142. The capillary 142 and the SAP 162 are both positioned in a channel 164 having a first region 166 and a second region 168. Using the glass capillary 142 and the SAP is similar to using a combination of a broken open valve and a self-close valve. The on-off-on valve 190 enables a user to control the flow of fluids through a particular location in the channel by allowing, then blocking, and then allowing fluids to pass through the particular location.

Referring to FIG. 9A, initially, the SAP 162 has a smaller volume and does not block the channel, allowing a fluid to flow between the first and second regions 166 and 168.

Referring to FIG. 9B, as the fluid passes, a portion of the fluid is absorbed by the SAP 162, causing the SAP 162 to increase in volume, blocking further flow of the fluid between the first and second regions 166 and 168.

Referring to FIG. 9C, when an external force is applied to break the glass capillary 142, a passage 152 is generated to allow the fluid to flow between the first and second regions 166 and 168.

Figure 10A:
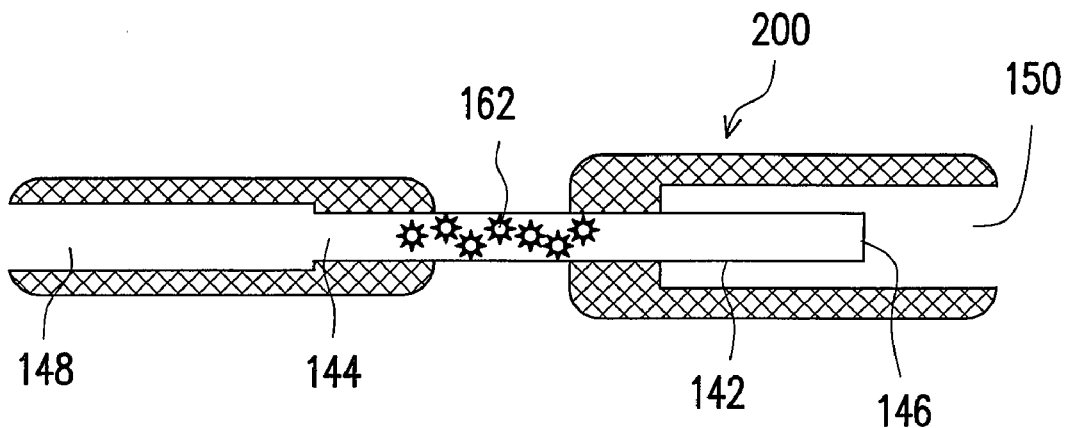
FIGS. 10A to 10C are schematic diagrams of an off-on-off valve.
Figure 10B:
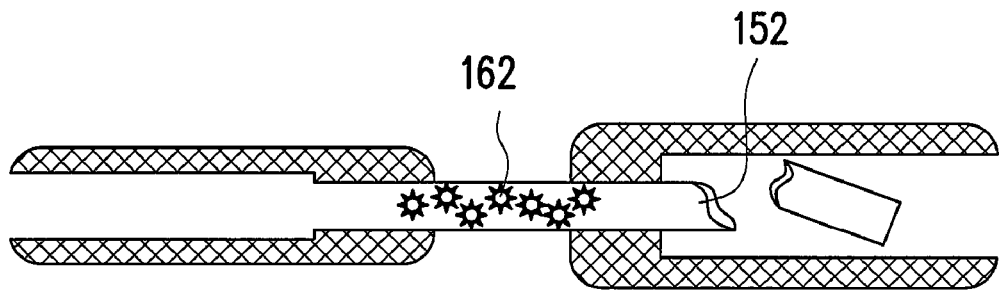
Figure 10C:
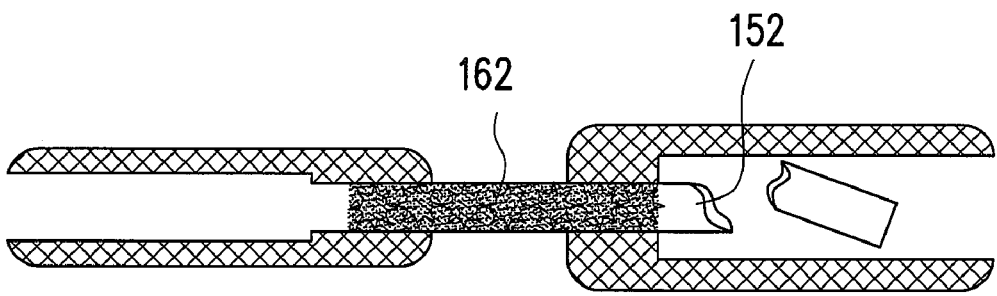

Referring to FIGS. 10A to 10C, an off-on-off valve 200 can be fabricated by using a glass capillary 142 and SAP 162 that are positioned inside the capillary 142. The capillary 142 has an open end 144 and a closed end 146. The open end 144 is positioned in a first channel 148, and the closed end 146 is positioned in a second channel 150. The glass capillary 142 and the SAP 162 perform functions similar to a combination of a broken open valve and a self-close valve. The off-on-off valve 200 enables a user to control the flow of fluids through a particular location in the channel by blocking, then allowing, and then blocking fluids to pass through the particular location.

Referring to FIG. 10A, when the glass capillary 142 is intact, the first and second channels 148 and 150 are not connected.

Referring to FIG. 10B, when an external force is applied to break the glass capillary 142, a passage 152 is formed, allowing fluid to flow between the channels 148 and 150. The SAP 162 initially has a smaller volume and does not block the flow of fluid in the passage 152.

Referring to FIG. 10C, as the fluid flows through the passage 152, a portion of the fluid is absorbed by the SAP 162, causing the SAP to increase in volume and block the passage 152, preventing further flow of the fluid through the passage 152.

Referring to FIGS. 11A to 11D, an on-off-on-off valve can be fabricated by using a glass capillary 142, SAP 212 that are positioned inside the capillary 142, and SAP 214 that are positioned outside of the capillary 142. The glass capillary 142, the SAP 212, and the SAP 214 are placed in a channel 164. The glass capillary 142, the SAP 212, and the SAP 214 perform functions similar to a combination of a broken open valve and two self-close valves. The on-off-on-off valve 210 enables a user to control the flow of fluids through a particular location in the channel by allowing, then blocking, then allowing, and then blocking fluids to pass through the particular location.

Figure 11A:
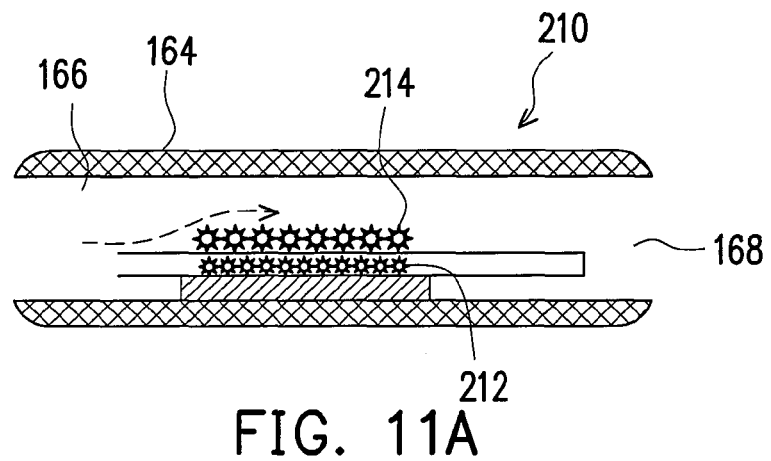
FIGS. 11A to 11D are schematic diagrams of an on-off-on-off valve.

Referring to FIG. 11A, initially, the SAP 214 has a smaller volume and allows a fluid to flow between a first region 166 and a second region 168 of the channel 164.

Figure 11B:
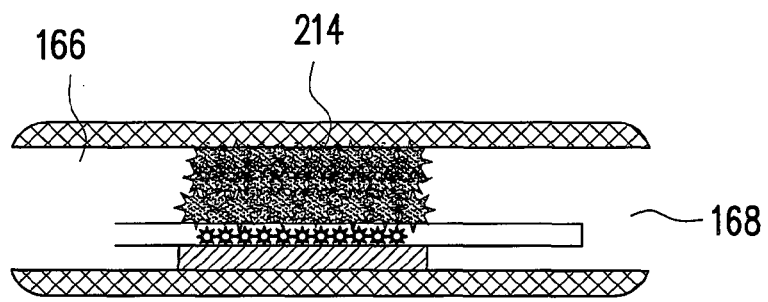

Referring to FIG. 11B, as fluid passes, a portion of the fluid is absorbed by the SAP 214, causing the SAP 214 to increase in volume, blocking further flow of the fluid between the first and second regions 166 and 168.

Figure 11C:
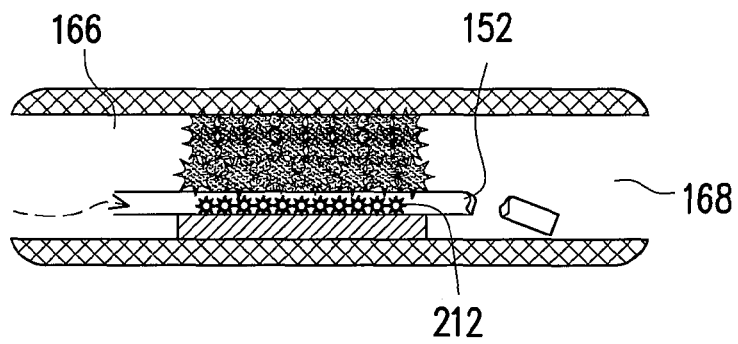

Referring to FIG. 11C, when an external force is applied to break the glass capillary 142, a passage 152 is formed to allow fluids to flow between the first and second regions 166 and 168.

Figure 11D:
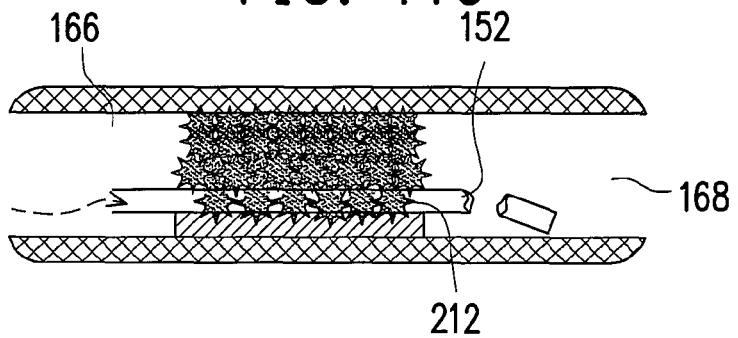

Referring to FIG. 11D, as the fluid flows pass the SAP 212, a portion of the fluid is absorbed by the SAP 212, causing the SAP 212 to increase in volume and block the passage 152, preventing further flow of fluids through the passage 152.

Figure 12:
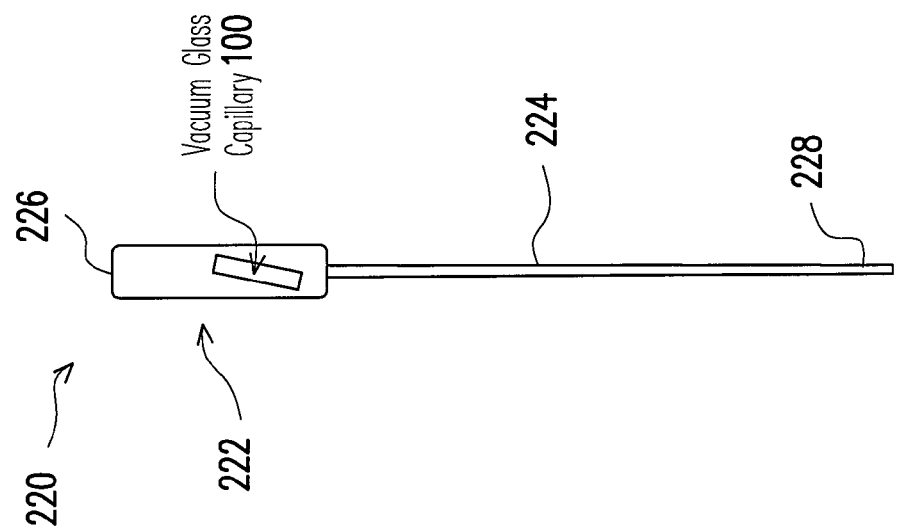
FIG. 12 is a schematic diagram of a metering pipette.

Referring to FIG. 12, a metering pipette 220 for drawing a predetermined amount of fluid can be constructed by using a vacuum pump 222 coupled to a pipette tube 224. The vacuum pump 222 includes a vacuum glass capillary 100 that is placed in a pipette bulb 226. To use the metering pipette 220, the glass capillary 100 is broken to generate a suction force that draws a fluid into the pipette tube 224.

When a batch of metering pipettes 220 are manufactured, the sizes of the bulb 226 and the glass capillary 100 can be made to be the same. The bulb 226 and the glass capillary 100 are designed so that when the user presses the bulb 226 to break the glass capillary 100, the amount of deformation imparted on the bulb 226 that is required to cause the glass capillary 100 to be broken is substantially the same for all the metering pipettes 220. This way, a user can use the metering pipette 220 to quickly draw in a predetermined amount of fluid without monitoring the fluid level in the stem 224.

Figure 21A:
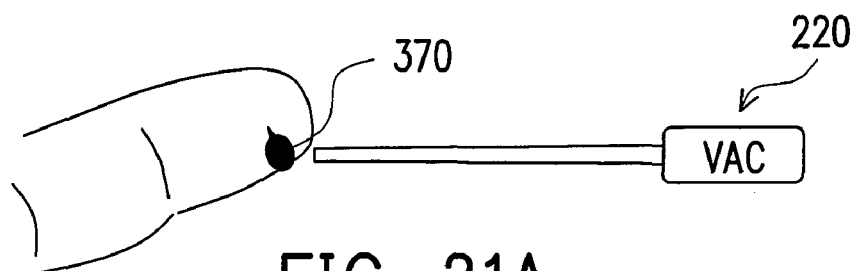
FIGS. 21A and 21B show a metering pipette being used to sample blood from a patient.
Figure 21B:
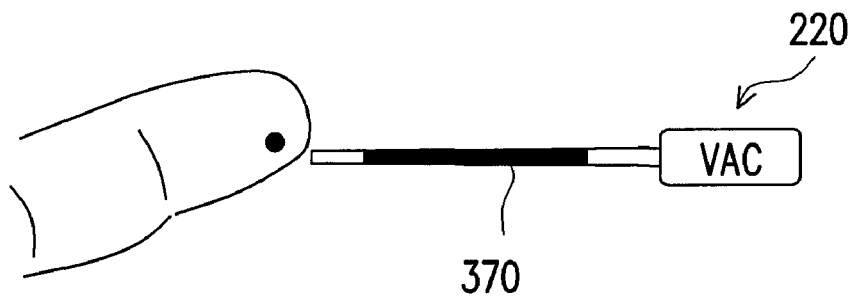

For example, referring to FIGS. 21A and 21B, a metering pipette 220 can be used to quickly sample a predetermined amount of blood 370 from a patient.

Figure 13:
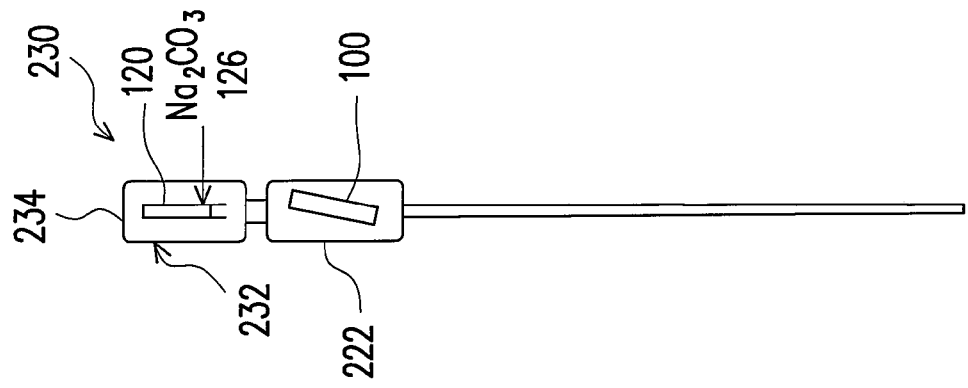
FIG. 13 is a schematic diagram of a metering pipette.

Referring to FIG. 13, another example of a metering pipette 230 includes a vacuum pump 222 and a gas pump 232. The vacuum pump 222 is similar to that shown in FIG. 12. The gas pump 232 includes a glass capillary 120 filled with $Na_2CO_3$ and placed in a pipette bulb 234 containing $CH_2COOH$. When the glass capillary 120 is broken, $Na_2CO_3$ interacts with $CH_2COOH$ to generate $CO_2$, increasing the gas pressure in the bulb 234. The vacuum pump 222 allows the user to quickly draw a predetermined amount of a fluid into the pipette 230. The gas pump 232 allows the user to dispense the fluid out of the pipette 230.

An advantage of using the gas pump 232 is that the fluid in the tube 228 can be dispensed over a controlled period of time as the $CO_2$ gas is generated from the reaction between $Na_2CO_3$ and $CH_2COOH$. This way, the user does not have to carefully monitor the output flow of the fluid when dispensing the fluid.

Figure 14C:
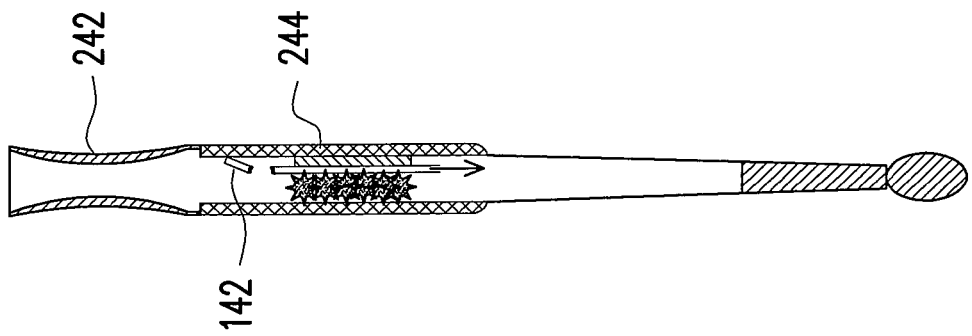
FIGS. 14A to 14C are schematic diagrams of a metering pipette.
Figure 14B:
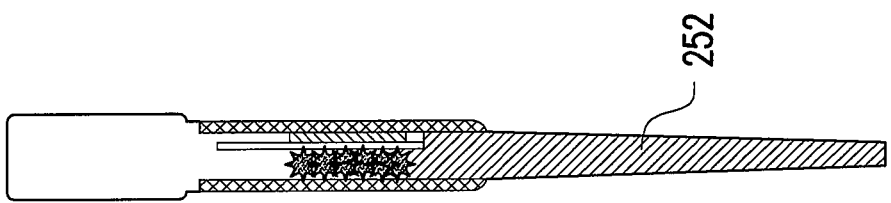
Figure 14A:
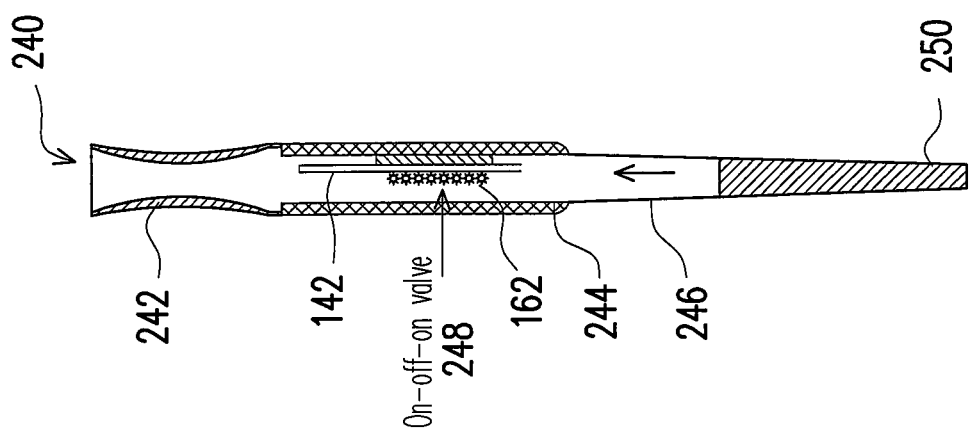

Referring to FIG. 14A, another example of a metering pipette 240 includes a bulb 242, a middle section 244, and a pipette tube 246. The middle section 244 is constructed of a deformable material. An on-off-on valve 248 is positioned in the middle section 244. The on-off-on valve 248 includes a glass capillary 142 and SAP 162 positioned outside of the capillary 142, similar to the device shown in FIGS. 9A to 9C.

Referring to FIG. 14A, to use the pipette 240, the user squeezes and releases the bulb 242 to draw a fluid into the tube 246 and the middle section 244.

Referring to FIG. 14B, when the fluid reaches the middle section 244 and comes into contact with the SAP 248, a portion of the fluid is absorbed by the SAP 248, causing the SAP 248 to expand in volume and block passage of the fluid beyond the SAP 248. This way, a predetermined amount of fluid is drawn into the pipette 240.

Referring to FIG. 14C, to dispense the fluid from the pipette 240, the user presses the middle section 244 (which is made of deformable material) to break the glass capillary 142, forming a passage through the broken capillary 142. The user then squeezes the bulb 242 to force the fluid out of the pipette 240.

When a batch of pipettes 240 are manufactured, the size of the tube 246 and the middle section 244, and the position of the on-off-on valves 248 within the middle section 244 are the same, so that users can use the pipettes 240 to quickly draw in substantially the same amounts of fluids without closely monitoring the levels of liquids in the pipettes 240.

Figure 15A:
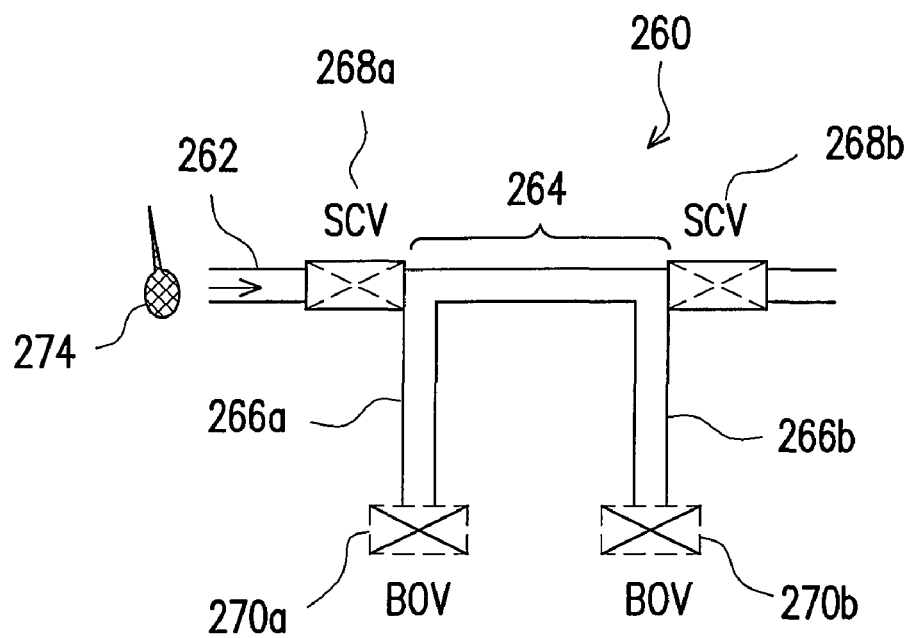
FIGS. 15A and 15B are schematic diagrams of a metering device.

Referring to FIG. 15A, a metering device 260 for collecting a predetermined amount of fluid includes a glass capillary 262 having two branches 266a and 266b, two self-close valves 268a and 268b, and two broken open valves 270a and 270b. Each of the self-close valves 268a and 268b has SAP that expands upon absorption of fluids. Initially, the self-close valves 268a and 268b are in the open state, and the broken open valves 270a and 270b are in the closed state. The self-close valves 268a and 268b can be similar to those shown in FIGS. 6A to 8C. The broken open valves 270a and 270b can be similar to those shown in FIGS. 5A and 5B.

Figure 15B:
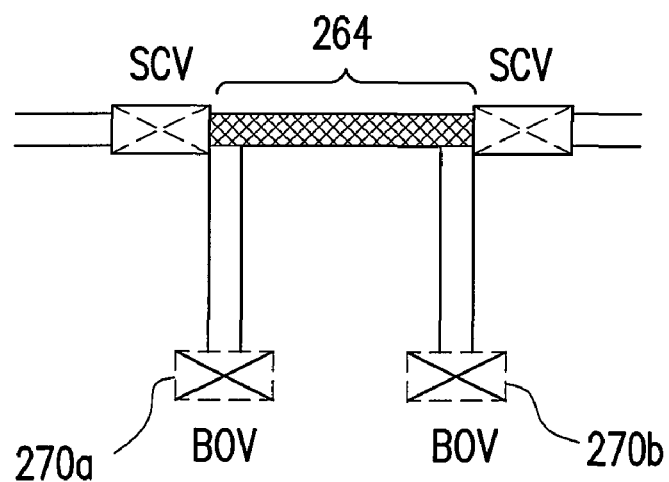

In operation, a fluid 274 is drawn into the capillary 262 due to a capillary force, and flows past the self-close valves 268a and 268b. Referring to FIG. 15B, as the fluid 274 flows pass the self-close valves 268a and 268b, a portion of the fluid 274 is absorbed by the SAP in the self-close valves 268a and 268b, causing the self-close valves 268a and 268b to change to the closed state, blocking further passage of the fluid 274. This results in the fluid 274 occupying a segment 264 of the capillary between the self-close valves 268a and 268b.

The fluid 274 can be moved from the segment 264 to other locations through the branch 266a or 266b by changing the broken open valves 270a and 270b from the closed state to the open state, and applying a suction force or a push force to move the fluid 274.

An advantage of the metering device 260 is that it can quickly sample a predetermined volume of fluid without careful monitor by the user. Because the capillary has a small diameter, the metering device 260 is useful in precisely sampling small amounts of fluid.

Figure 16A:
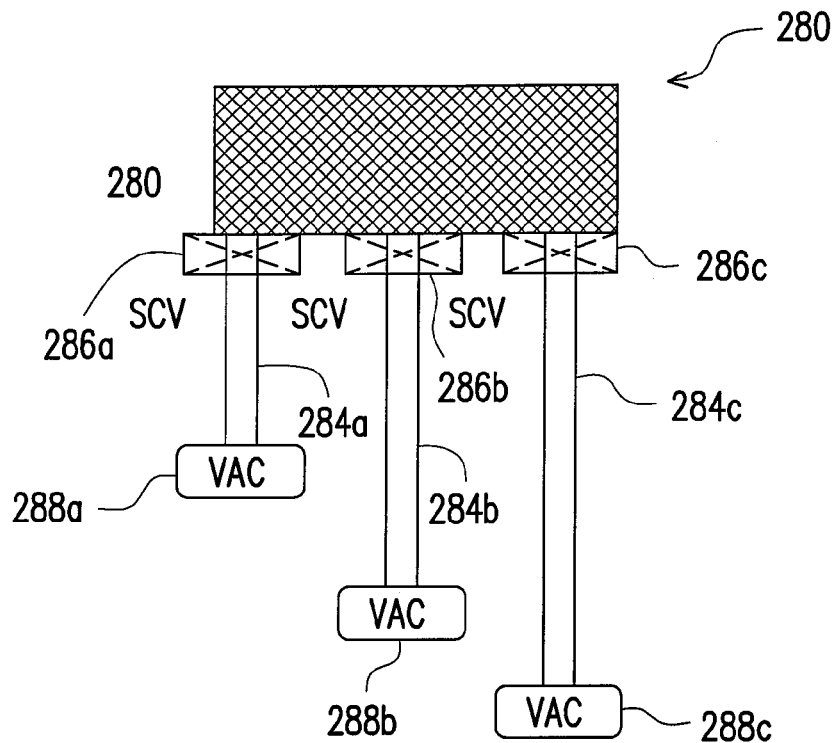
FIGS. 16A and 16B are schematic diagrams of a metering device.

Referring to FIG. 16A, a metering device 280 that can obtain three different amounts of fluids from a sample well 282 includes three capillaries 284a, 284b, and 284c. Each capillary has a self-close valve (e.g., 286a, 286b, or 286c) at one end and a vacuum valve (e.g., 288a, 288b, or 288c) at the other end. Each vacuum pump has a vacuum glass capillary. Initially, the self-close valves are in the open state.

Figure 16B:
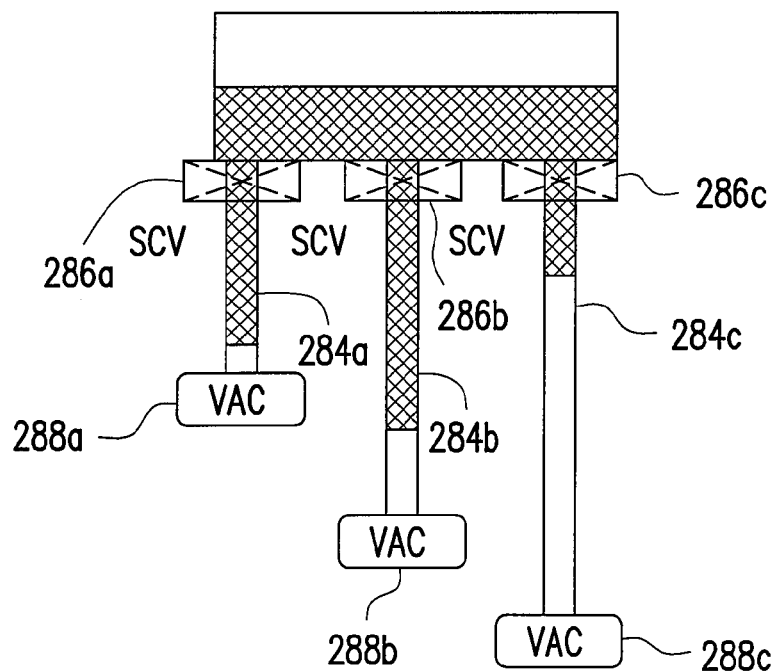

Referring to FIG. 16B, when the user breaks the vacuum glass capillary in the vacuum pumps 288a, a suction force is generated to draw a predefined amount of liquid into the capillary 284a. As the fluid passes the self-close valve 286a, the SAP in the self-close valve 286a expands, causing the self-close valve 286a to enter the closed state, preventing further movement of the fluid through the self-close valve 284a. Similarly, predefined amounts of fluid can be drawn into the capillaries 284b and 284c by breaking the vacuum capillaries in the vacuum pumps 288b and 288c. The amounts of fluid drawn into the capillaries 284a to 284c are determined by the volumes of the capillaries in the vacuum pumps 288a to 288c, which can be the same or different.

Figure 17C:
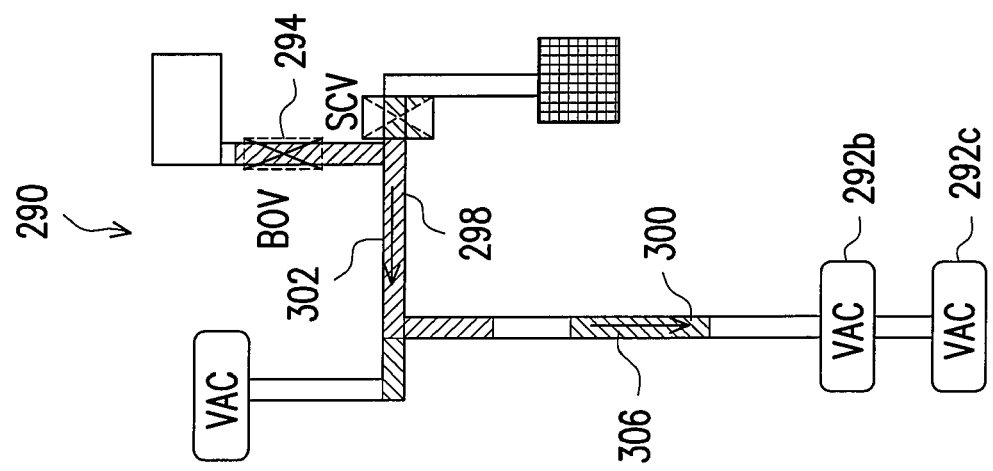
FIGS. 17A to 17C are schematic diagrams of a device for use in a two-step assay.
Figure 17B:
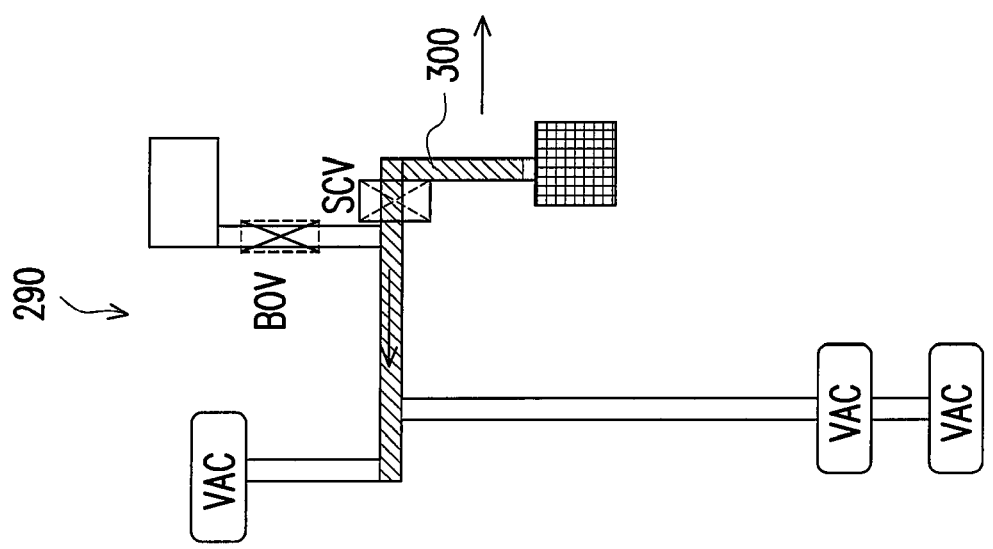
Figure 17A:
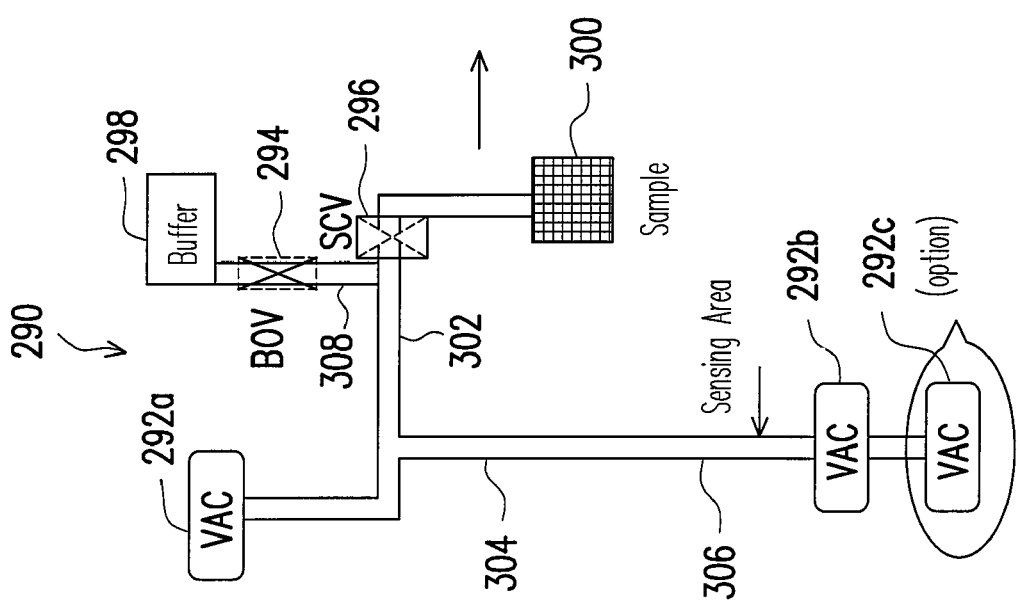

Referring to FIG. 17A, a device 290 for use in a two-step assay that requires rapid binding of reagents followed by washing with a buffer can be fabricated using a combination of vacuum pumps, a broken-open valve, and a self-close valve. A channel 302 has one end coupled to a sample well 300 through a self-close valve 296, and another end coupled to a first vacuum pump 292a. The channel 302 is connected to a channel 308, which is coupled to a buffer 298 through a broken-open valve 294. The channel 302 is also connected to a channel 304, which is coupled to a second vacuum pump 292b and a third vacuum pump 292c. The channel 304 includes a binding and/or sensing area 306 that includes reagents for binding or sensing compounds in the sample 300.

The device 290 is operated in a way such that the sample 300 is drawn towards the binding and sensing area 306 to cause a reaction to occur, then the buffer 298 is drawn towards the binding and sensing area 306 to wash the binding and sensing area 306.

Referring to FIG. 17B, the vacuum pump 292a is activated to generate a suction force that draws the sample 300 towards the vacuum pump 292a and into the section of the channel 302 between the vacuum pump 292a and the self-close valve 296. As the sample 300 flows past the self-close valve 296, a portion of the sample is absorbed by the SAP in the self-close valve 296, causing the self-close valve 296 to enter the closed state.

Referring to FIG. 17C, the broken-open valve 294 is activated to cause the valve 294 to change to the open state. The vacuum pump 292b is activated to generate a suction force that draws both the sample 300 and the buffer 298 towards the vacuum pump 292b. The vacuum pumps 292a and 292b are designed such that after the pumps are activated, the sample 300 will stop at the binding and sensing area 306. After a period of time, the vacuum pump 292c is activated to move the sample 300 out of the area 306, and cause the buffer 298 to flow through and wash the area 306.

The example above provides incubation time that allows the compounds in the sample 300 to react with the reagents in the binding and sensing area 306 before the area 306 is washed by the buffer 290. If the reactions at the area 306 is fast and incubation time is not necessary, then the vacuum pump 292b can be made larger and the vacuum pump 292c can be omitted. When the vacuum pump 292b is activated, the sample rapidly flows pass the binding and sensing area 306, followed by washing by the buffer 298.

Figures 18A, 18B, 18C:
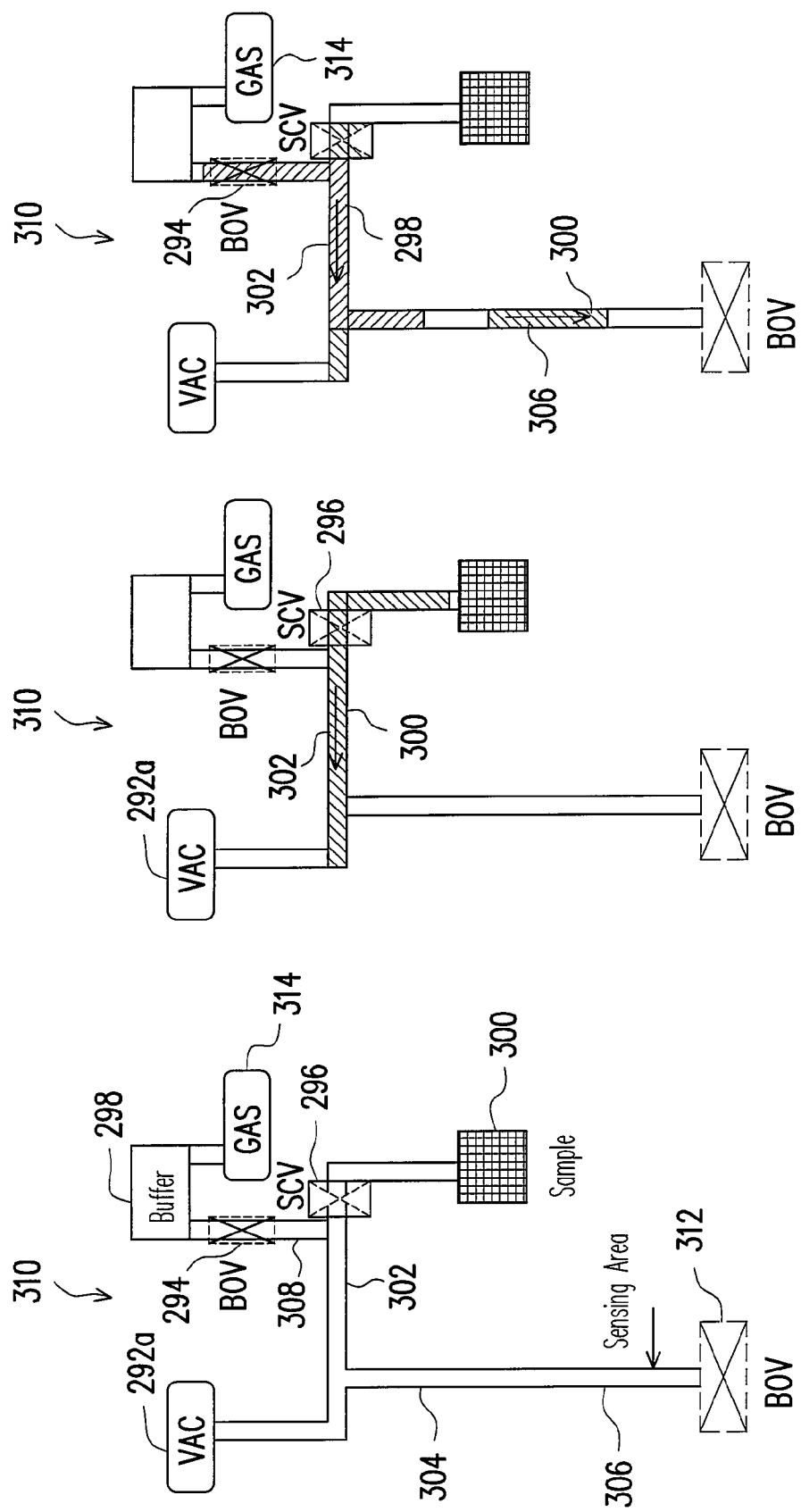
FIGS. 18A to 18C are schematic diagrams of a device for use in a two-step assay.

Referring to FIG. 18A, a device 310 for use in a two-step assay that requires slow binding of reagents followed by washing with a buffer can be fabricated using a combination of a vacuum pump, broken-open valves, a self-close valve, and a gas pump. The device 310, similar to the device 290, has a channel 302 connected to two channels 304 and 308. The channel 302 is coupled to a sample 300 through a self-close valve 296. The channel 308 is coupled to a buffer 298 through a broken-open valve 294. The channel 304 includes a binding and sensing area 306. One end of the channel 304 is coupled to a broken-open valve 312. A gas pump 314 is coupled to the buffer 298.

The difference between the device 310 and the device 290 is that, in device 310, rather than using the vacuum pump 292b to draw the sample 300 and buffer 298 towards the binding and sensing area 306, the gas pump 314 is used to push the sample 300 and the buffer 298 towards the area 306.

Referring to FIG. 18B, to perform the two-step assay, the vacuum pump 292a is activated to draw the sample 300 into the channel. The self-close valve 296 enters a closed state after the sample flows pass the valve 296.

Referring to FIG. 18C, the broken-open valves 294 and 312 are activated to cause the valves to change to the open state. The gas pump 314 is activated to generate gas over a period of time, pushing the sample 300 and the buffer 298 through the binding and sensing area 306. Because the gas pump 314 generates gas over a period time (the reaction between compounds that generate gas takes a certain amount of time to complete), the sample 300 can pass the binding and sensing area 306 slowly, allowing slow binding reactions to occur.

Referring to FIG. 19A, a device 320 for use in a three-step assay that requires rapid binding of reagents followed by washing with two buffers can be constructed by adding a second buffer 324, and a channel 322 to the structure show in FIG. 17A. To perform the multi-step assay, the vacuum pump 292a is activated to cause the sample 300 to flow to the channel 302. As the sample 300 flows past the self-close valve 296, the valve 296 changes to a closed state.

Referring to FIG. 19B, the broken-open valve 294 is activated so that it changes to an open state, and the vacuum pump 292b is activated to cause the sample 300 and the first buffer 298 to be drawn towards the binding and sensing area 306.

Referring to FIG. 19C, the broken-open valve 326 is activated so that it changes to an open state, and the vacuum pump 292c is activated to cause the sample 300, the first buffer 298, and the second buffer 324 to be drawn towards the binding and sensing area 306. This way, the reaction at the area 306 can be washed by two different buffers.

A device for use in assays that require more than three steps can be constructed by coupling additional buffers or samples, and adding a corresponding number of vacuum pumps to the end of the channel 304.

Figure 20:
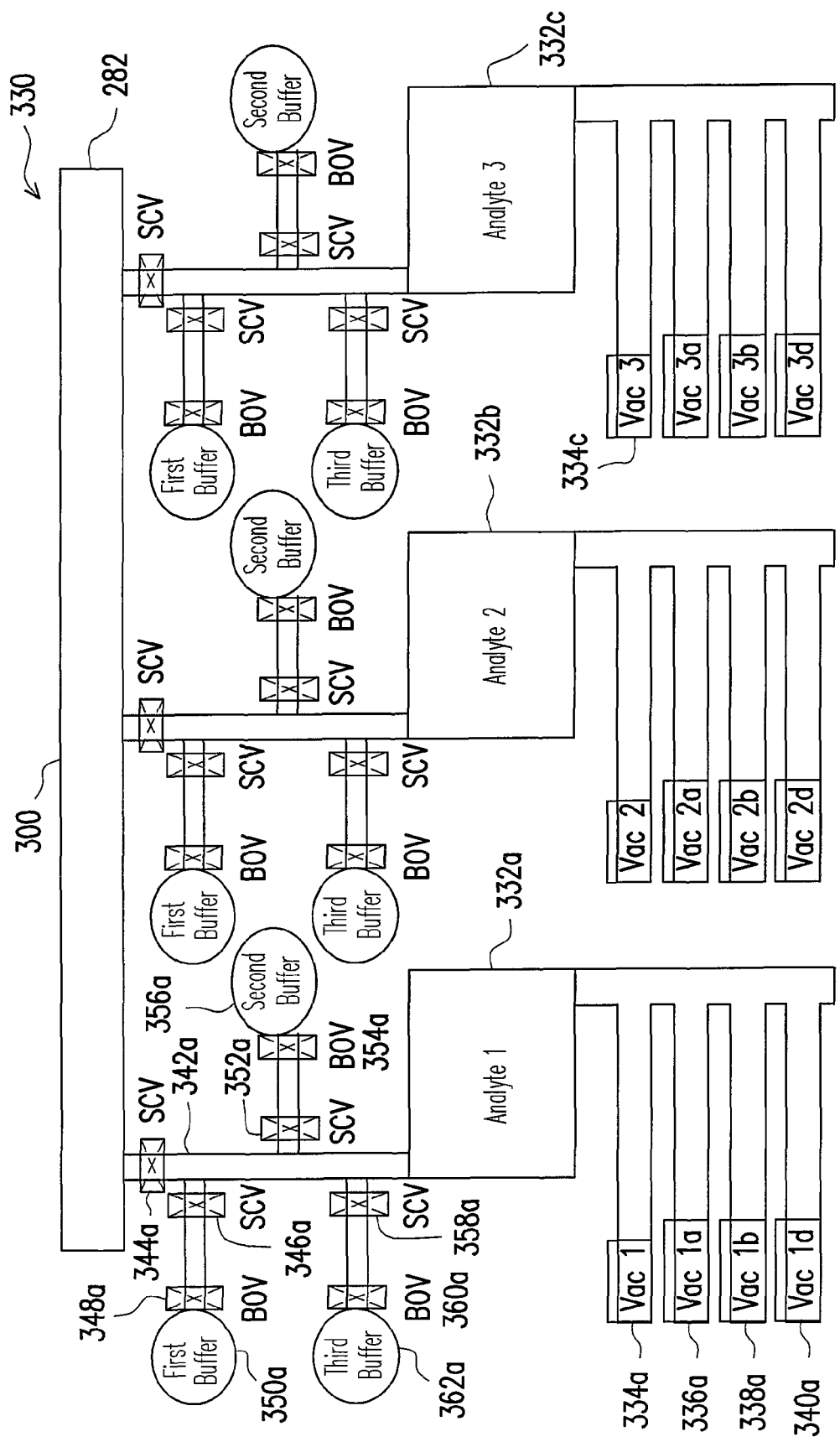
FIG. 20 is a schematic diagram of a module for use in a multiplex analyte assay.

Referring to FIG. 20, a module 330 can be constructed to perform multiplex analyte assay. The module includes a sample well 282 for holding a sample 300 and three chambers 332a, 332b, and 332c, each containing an analyte for binding and sensing compounds in the sample 300. Below is a description of the components used to perform an assay concerning the first analyte in the chamber 332a.

The chamber 332a is coupled to the sample well 282 through a channel 342a and a self-close valve 344a. The channel 342a is coupled to a first buffer 350a through a self-close valve 346a and a broken-open valve 348a. The channel 342a is coupled to a second buffer 356a through a self-close valve 352a and a broken-open valve 354a. The channel 342a is coupled to a third buffer 362a through a self-close valve 358a and a broken-open valve 360a. The chamber 332a is also connected to vacuum pumps 334a, 336a, 338a, and 340a.

To perform the assay, the vacuum pump 334a is activated to draw the sample 300 towards the chamber 332a to allow the compounds in the sample 300 to react with the analyte 332a. After a certain amount of the sample flows through the self-close valve 344a, the valve 344a changes to the closed state. The first buffer 350a is flushed through the chamber 332a by activating the broken-open valve 348a (to change the valve to the open state) and the second vacuum pump 336a. After a certain amount of the first buffer 350a flows past the self-close valve 346a, the valve 346a changes to a closed state.

The second buffer 356a is flushed through the chamber 332a by activating the broken-open valve 354a (to change the valve to the open state) and the third vacuum pump 338a. After a certain amount of the second buffer 356a flows past the self-close valve 352a, the valve 352a changes to a closed state.

In a similar manner, the third buffer 362a is flushed through the chamber 332a by activating the broken-open valve 360a (to change the valve to the open state) and the third vacuum pump 340a. After a certain amount of the third buffer 362a flows past the self-close valve 358a, the valve 358a changes to a closed state.

The assays concerning the second and third analytes in the chambers 332b and 332c can be performed similar to the manner that the assay concerning the first analyte in the chamber 332a is performed. The assays concerning the first, second, and third analytes in the chambers 332a, 332b, and 332c can be performed simultaneously.

The following are applications of the vacuum pumps and gas pumps in performing biological assays.

Figure 22A:
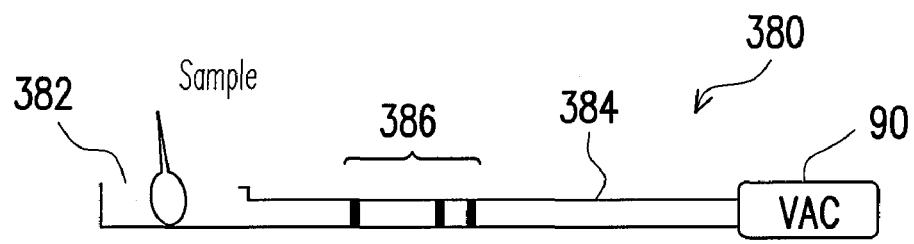
FIGS. 22A and 22B are schematic diagrams of a device for performing rapid reaction colorimetric assay.
Figure 22B:
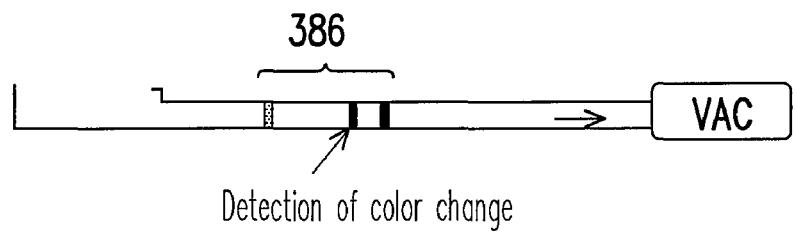

FIGS. 22A and 22B show a device 380 for performing rapid reaction calorimetric assay. The device 380 includes a channel 384 coupled to a sample well 382 at one end and a vacuum pump 90 at the other end. The sample well 382 can hold a fluid, such as blood or urine. The channel 384 includes a testing area 386 having test lines that change color upon detection of certain compounds. The vacuum pump 90 when activated can quickly draw the fluid in the sample well 382 through the testing area 386. By reading the color of the test lines, a user can quickly determine the existence or non-existence of certain compounds in the fluid.

FIGS. 23A and 23B show a device 390 for sampling a filtered fluid. The device 390 includes a channel 384 that has one end coupled to a sample well 382 and another end coupled to a vacuum pump 90. A filter membrane 392 is placed in the sample well 382. The vacuum pump 90 when activated can quickly draw a fluid (e.g., blood) in the sample well 382 through the filter membrane 392, producing a filtered fluid (e.g., plasma) that is drawn into the channel 384.

FIGS. 24A to 24C show a device 400 for performing a slow colorimetric assay. The device 400 includes a sample well 402 coupled between a gas pump 404 and a channel 384. The channel 384 has a test area 386 having test lines that change color upon detection of certain compounds. To use the device 400, a sample fluid 406 is placed in the sample well 402. A sealing tape 408 seals the opening of the sample well. The gas pump 404 is activated to generate gas that pushes the sample fluid 406 through the test area 386. Because the gas pump 404 generates gas over a period of time, the sample fluid 406 travels through the test area over a period of time, allowing a slow colorimetric assay to be performed.

In an embodiment of the present invention, referring to FIGS. 29A and 29B, a device 500 for performing an antibody assay on a blood sample is manufactured by a combination of a self-close valve (SLV) and a broken open valve (BOV). The device 500 comprises a blood sample well 501, a washing buffer well 503, a metering zone and labeled antibody zone 505, a diagnostic zone (antibody array) 507, a broken open valve (BOV) 509, a waste well 511, and a self-close valve (SLV) 513. The metering zone and labeled antibody zone 505 have a channel connecting the blood sample well 501 with the washing buffer well 503, and the self-close valve (SLV) 513 is in the channel. The diagnostic zone 507 has another channel, which connects a center of the metering zone and labeled antibody zone 505 with the waste well 511 through the broken open valve (BOV) 509.

Figure 30B:
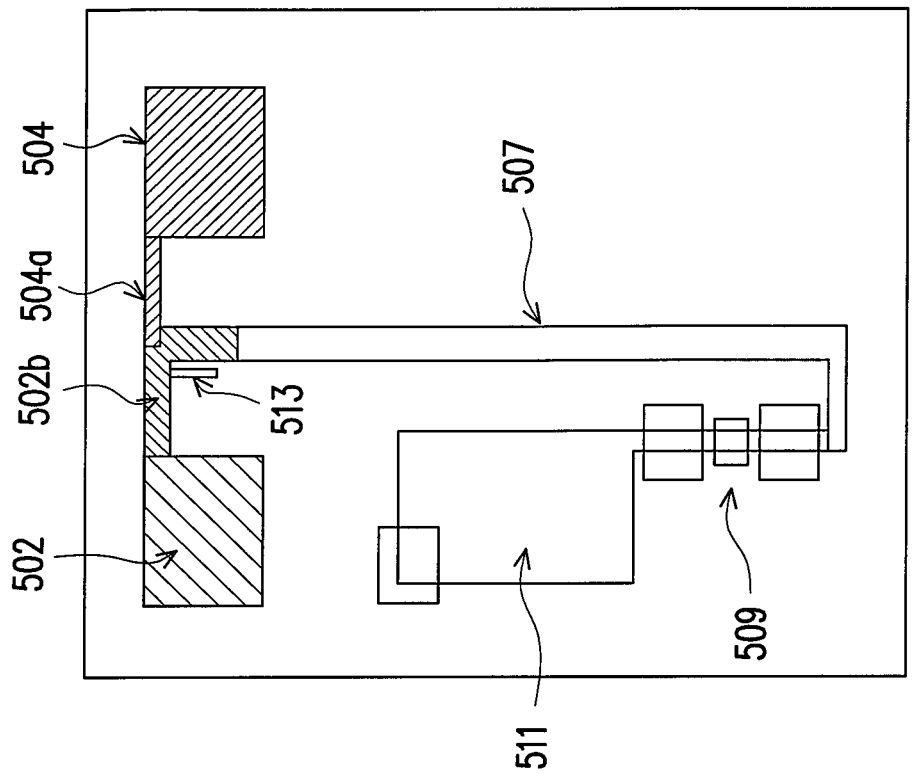
FIGS. 30A to 30C are diagrams showing an operation of the device in FIG. 29A.
Figure 30A:
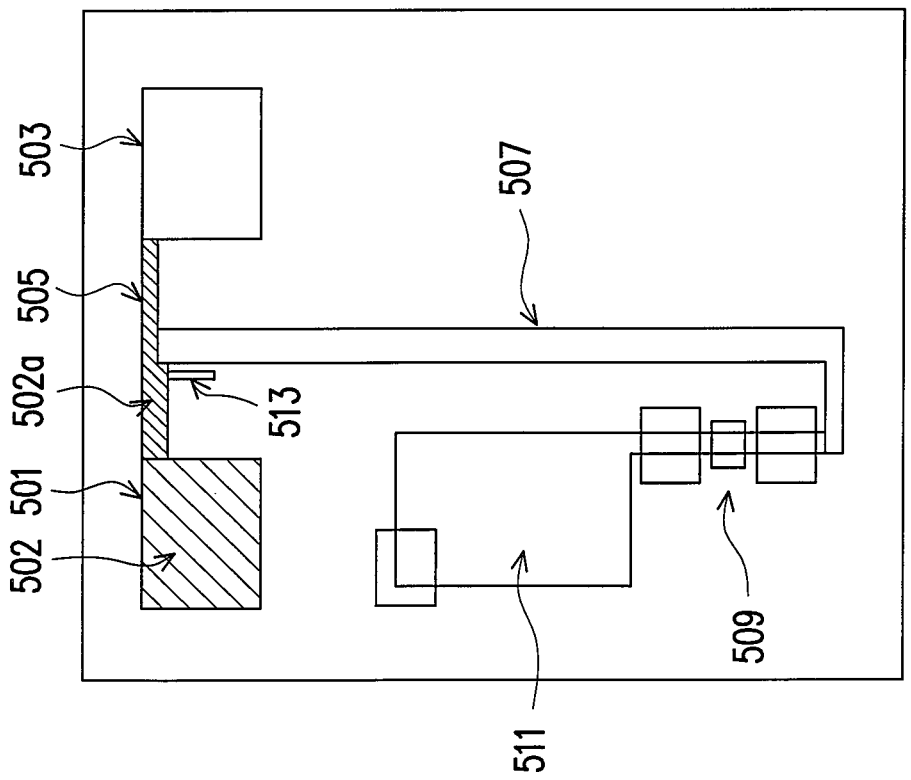
Figure 30C:
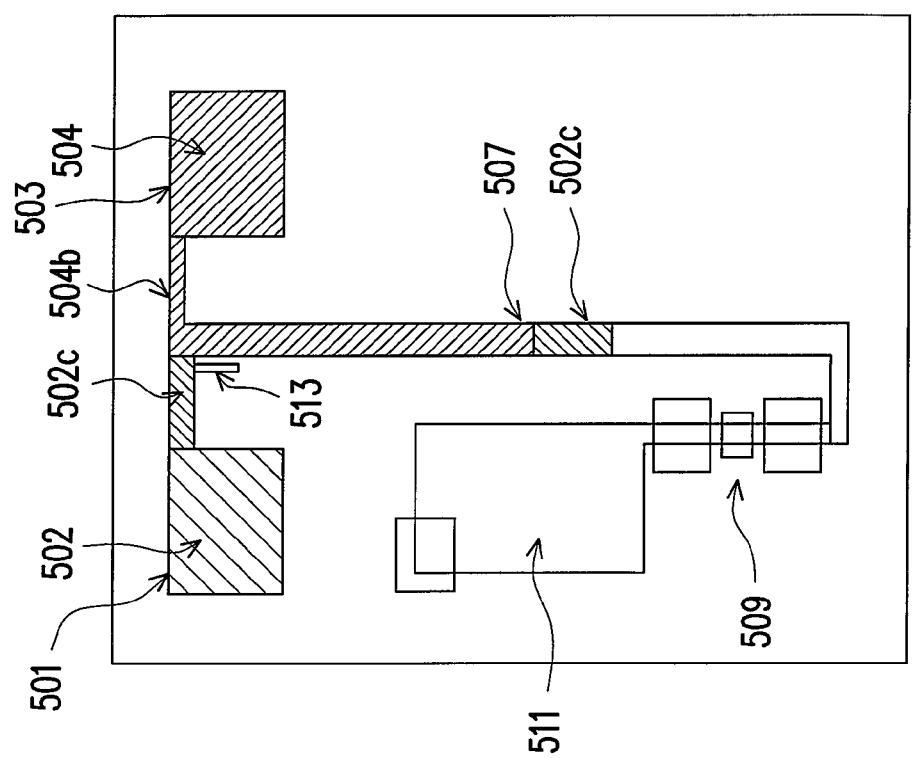

A method, by which the device 500 performs an antibody assay on a blood sample, is shown in FIGS. 30A, 30B, and 30C. First, referring to 502a in FIG. 30A, a blood sample 502 is infused into the blood sample well 501, and the self-close valve (SLV) 513, mentioned in aforesaid embodiment of the present invention, is used to pull a blood into the channel of the metering zone and labeled antibody zone 505 by a capillary force. Then, referring to 504a in FIG. 30B, a washing buffer solution is infused into the washing buffer well 503 and flows into the channel of the metering zone and labeled antibody zone 505. Simultaneously, the blood is pushed into the diagnostic zone 507, shown as 502b in FIG. 30B.

Referring to FIG. 30C, the blood is further pulled through the diagnostic zone 507 after the broken open valve (BOV) 509 is activated, shown as 502c in FIG. 30C. Simultaneously, an antigen in the blood interacts with an antibody array in the diagnostic zone 507, and uninteracted blood is flushed into the waste well 511 by the washing buffer solution.

Figure 31:
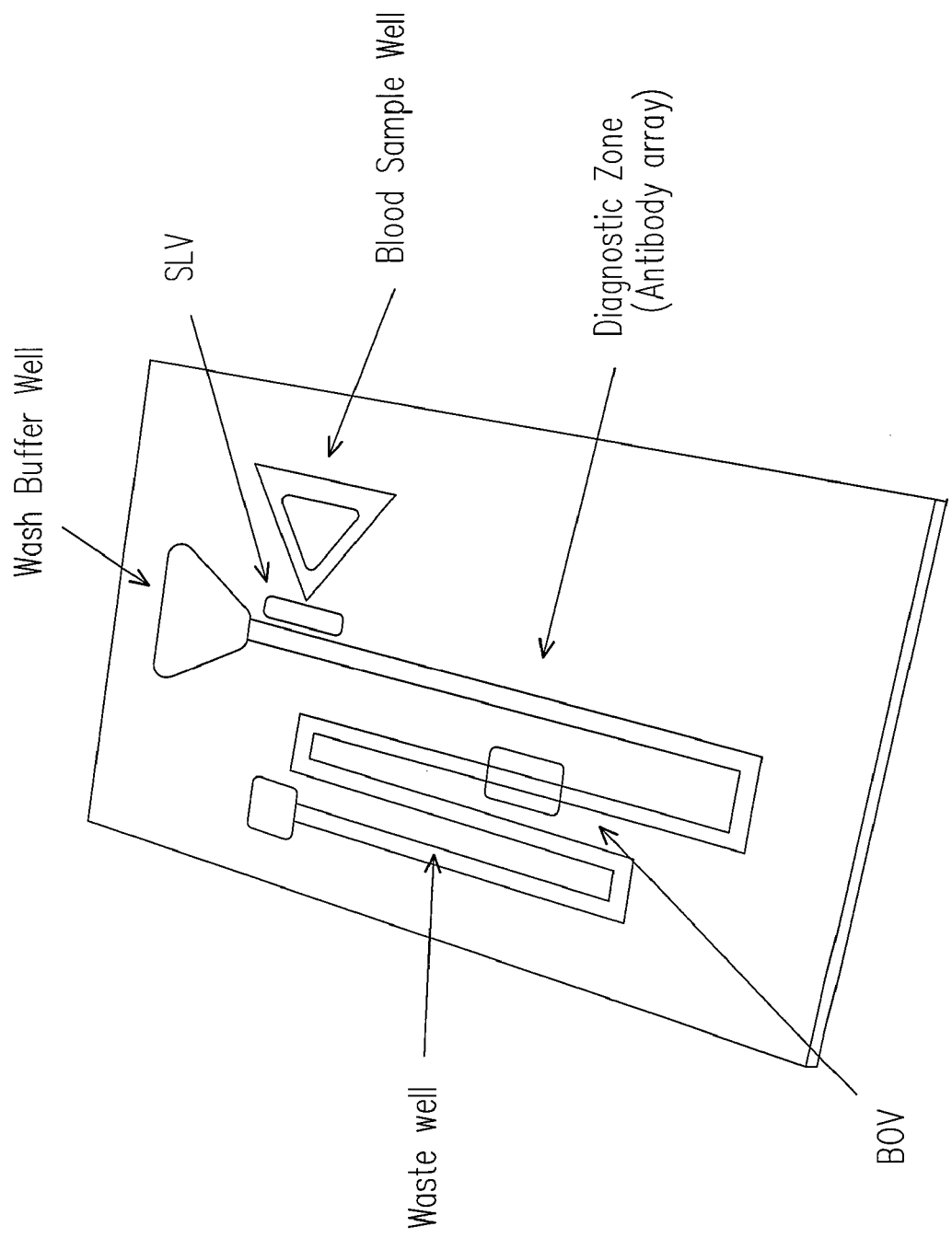
FIG. 31 shows a device in another embodiment of the present invention, which is manufactured by a combination of a self-close valve (SLV) and a broken open valve (BOV) to perform an antibody assay of a blood sample.

Please refer to FIG. 31 for another embodiment of the present invention. A device for performing an antibody assay on a blood sample is manufactured by a combination of a self-close valve (SLV) and a broken open valve (BOV). The device comprises a blood sample well, a washing buffer well, a diagnostic zone (with an antibody array therein), a broken open valve (BOV), a waste well, and a self-close valve (SLV). The blood sample well comprises a film for blood cell removal, which removes blood cells when a blood sample is pulled through.

The diagnostic zone has a channel, which connects the blood sample well with the washing buffer well, and connects to the waste well through the broken open valve (BOV). The self-close valve (SLV) is disposed at the joint of the blood sample well and the channel, which controls a blood volume flowing into the diagnostic zone and prevents the blood from flowing back to the blood sample well.

After the broken open valve (BOV) is activated, the blood is pulled through the film for blood cell removal and flows into the diagnostic zone. Simultaneously, an antigen in the blood interacts with an antibody array in the diagnostic zone, and uninteracted blood is flushed into the waste well by the washing buffer solution.

Aforesaid superabsorbent polymer (SAP) absorbs and retains large volumes of water or other aqueous solutions. In some examples, SAP can be made from chemically modified starch and cellulose and other polymers, such as poly (vinyl alcohol) PVA, poly (ethylene oxide) PEO, which are hydrophilic and have a high affinity for water. In some examples, superabsorbent polymers can be made of partially neutralized, lightly cross-linked poly (acrylic acid), which has a good performance versus cost ratio.

When the superabsorbent polymer is used in the self-close valve, it is preferable to use a vacuum pump because a gelling time of the superabsorbent polymer is about several seconds. Under a capillary force and a centrifugal force, a flowing speed of a fluid is less than the gelling time of SAP. Therefore, the flow of the fluid is stopped, and the flow of the fluid in the channel is also stopped. Hence, by adding a time lag layer, a "close" time of the self-close valve of the present invention is delayed. In addition, the time lag layer is manufactured by using a material which does not affect a sample so as to achieve the applications requiring slow flowing speed. The time lag layer is hereby called a time lag valve.

In the embodiment, a soluble material is disposed in a channel of the self-close valve, between the superabsorbent polymer SAP and the fluid. When an assay solution flows through the channel, a speed, which the superabsorbent polymer absorbs and retains large volumes of water or other aqueous solutions, is delayed by the soluble material, and the gelling time is therefore slowed to meet the requirement of slow flowing speed.

Figure 32A:
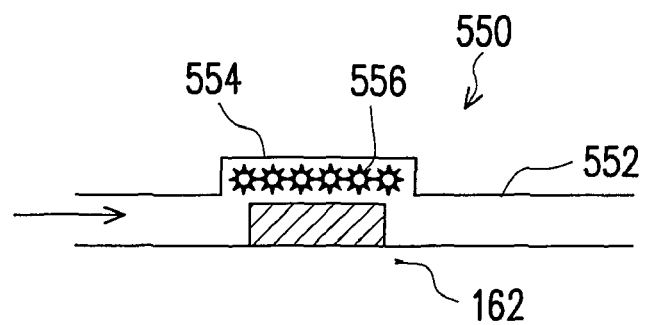
FIGS. 32A and 32B show a self-close valve having a lag layer.
Figure 32B:

Referring to FIG. 32A, a self-close valve 550 comprises a channel 552, which has an expanded section 554 for containing a superabsorbent polymer 556 so that a fluid is not blocked by unexpanded superabsorbent polymer 556. The self-close valve 550 is produced by applying an adhesive onto an inner surface of the expanded section 554 and then adhering powdered SAP 556 onto the inner surface of the expanded section 554 through pushing powdered SAP 556 into the channel 552. A lag layer 558 made of a soluble material is disposed in a channel of the expanded section 554 of the channel 552. Referring to 32B, when a fluid flows through, the superabsorbent polymer 556 starts absorbing a volume of the fluid and expands to block the channel 552 after the lag layer 558 dissolves.

A material of the lag layer is mainly a soluble material. In an embodiment, a suitable water-soluble material is, for example, a sugar cube or a sugar sheet, disposed between the channel and the superabsorbent polymer (SAP), and the thickness of the sugar cube or the sugar sheet is 0.01~2 mm. When a water-soluble solution flows through the channel, the water-soluble solution dissolves a sugar and prevents the SAP absorbing water. As the sugar dissolves, the superabsorbent polymer is allowed to start absorbing water and expand. After the sugar completely dissolves, the superabsorbent polymer completely blocks the channel and a "close" process is finished. A lag time is determined by the thickness of the sugar, which is variable according to requirements. Moreover, the lag time is also determined by a material of the lag layer.

Figure 33A:
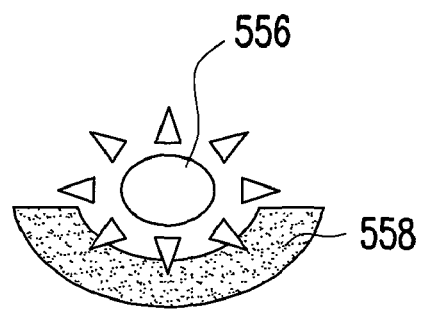
FIGS. 33A and 33B respectively show a partial coating and a whole coating.
Figure 33B:
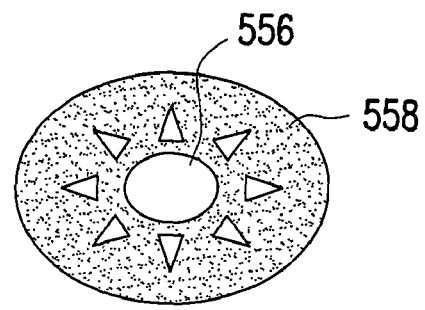

In another embodiment, the channel 552 of the self-close valve 550 does not require the expanded section 554, and powdered superabsorbent polymer 556 is adhered onto an inner surface of the channel 552 instead. After a SAP material is formed by powdered superabsorbent polymer 556, a process of dip-coating, roll coating, or spin coating of melted sugar is performed to mix a lag layer material with powdered superabsorbent polymer 556. FIGS. 33A and 33B respectively illustrate a partial coating and a whole coating. Meanwhile, a speed, which the SAP material absorbs and retains a large volume of water or other aqueous solutions, decreases so as to achieve the same effect.

Figure 34A:
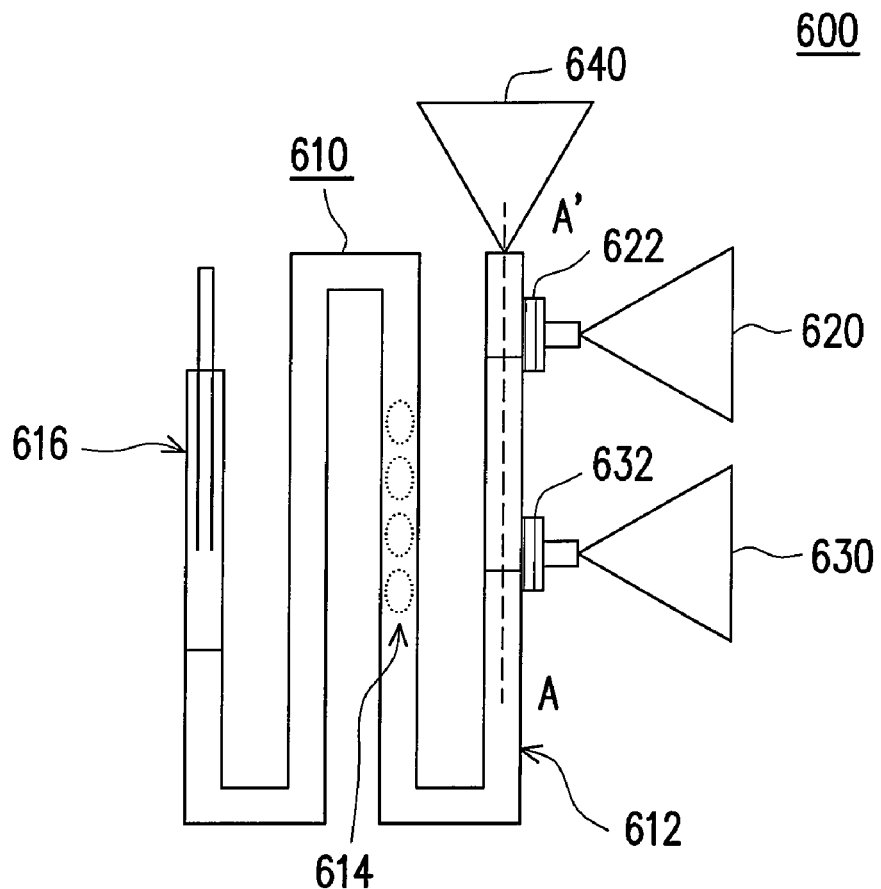
FIGS. 34A and 34B show an antibody assay device in an embodiment of the present invention, which has a time lag valve.
Figure 34B:
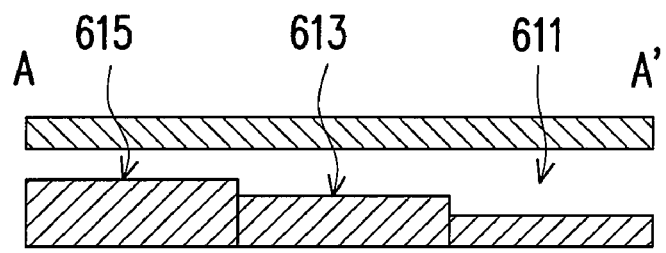

Aforesaid time lag valve is applicable in a plurality of examples, such as an antibody assay device shown in FIGS. 34A and 34B. An antibody assay device 600 comprises a specimen channel 610, a labeled antibody well 620 connected with the specimen channel 610, a sample well 630, and a washing buffer well 640. A time lag valve 622 is disposed between the specimen channel 610 and the labeled antibody well 620, and a time lag valve 632 is disposed between the specimen channel 610 and the sample well 630. The specimen channel 610 comprises a step area 612, an antibody array area 614, and a broken open valve 616.

The step area 612 is coordinated with the time lag valves 622 and 632. As shown in a AA' schematic cross-sectional view of FIG. 34B, a diameter of the specimen channel 610 is a step-like design. A large diameter 611 is changed to a smaller diameter 613, and then changed to an even smaller diameter 615. The decreasing diameter of the channel enhances a capillary force at the channel end. Moreover, by using the step design and the time lag valves 622 and 632, the fluid is maintained at a certain volume when flowing into the specific channels.

FIGS. 35A to 35D show a process flow for performing an antibody assay on a blood sample by using the antibody assay device 600 illustrated in FIG. 34A. The antibody assay device 600 comprises an specimen channel 610, a labeled antibody well 620, a sample well 630, a washing well 640, a first time lag valve 622, and a second time lag valve 632. The specimen channel 610 comprises a step area 612, an antibody array 614, and a broken open valve 616. The step area 612 comprises an area 611, an area 613, and an area 615, which have different diameters. The area 611 has a larger diameter, and the area 613 has a smaller diameter, for example, smaller than the diameter of the area 611.

Figure 35A:
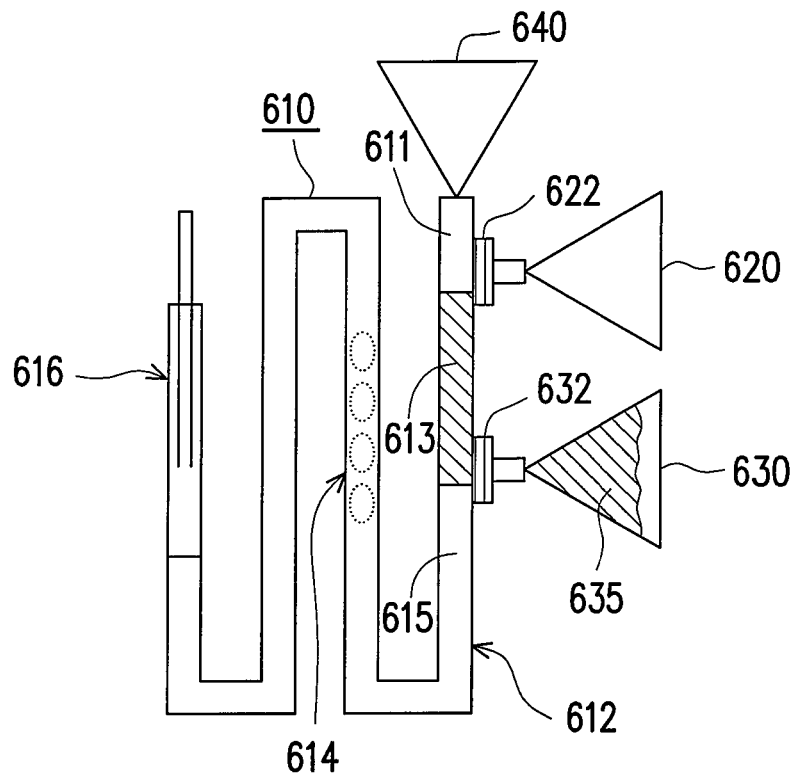
FIGS. 35A to 35D show an antibody essay method, which has a time lag valve.

Referring to FIG. 35A, a blood sample 635 is infused into the sample well 630 and then flows at a slow speed through the second time lag valve 632 to the area 613. Thereafter, the second time lag valve 632 closes to stop the blood sample 635 from flowing into the specimen channel 610. Because the diameter of the area 613 of the specimen channel 610 is fixed, a certain volume of the blood sample 635 is obtained.

Figure 35B:
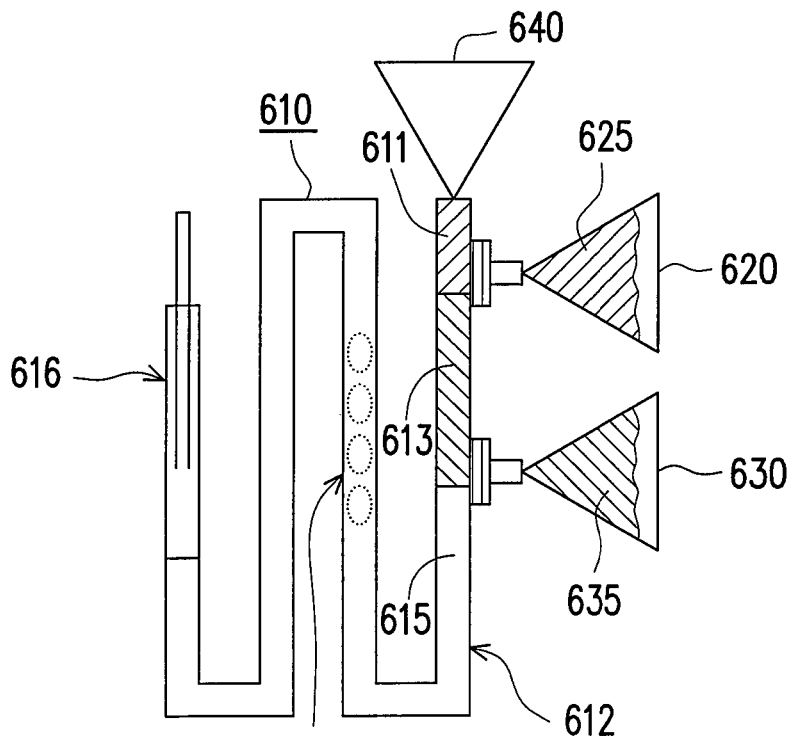

Then, referring to FIG. 35B, a labeled antibody 625 is infused into the labeled antibody well 620 and then flows at a slow speed through a first time lag valve 622 to the area 611. Thereafter, the first time lag valve 622 closes to stop the labeled antibody 625 flowing into the specimen channel 610. Because the diameter of the area 611 of the specimen channel 610 is fixed, a certain volume of the labeled antibody 625 is obtained.

Figure 35C:
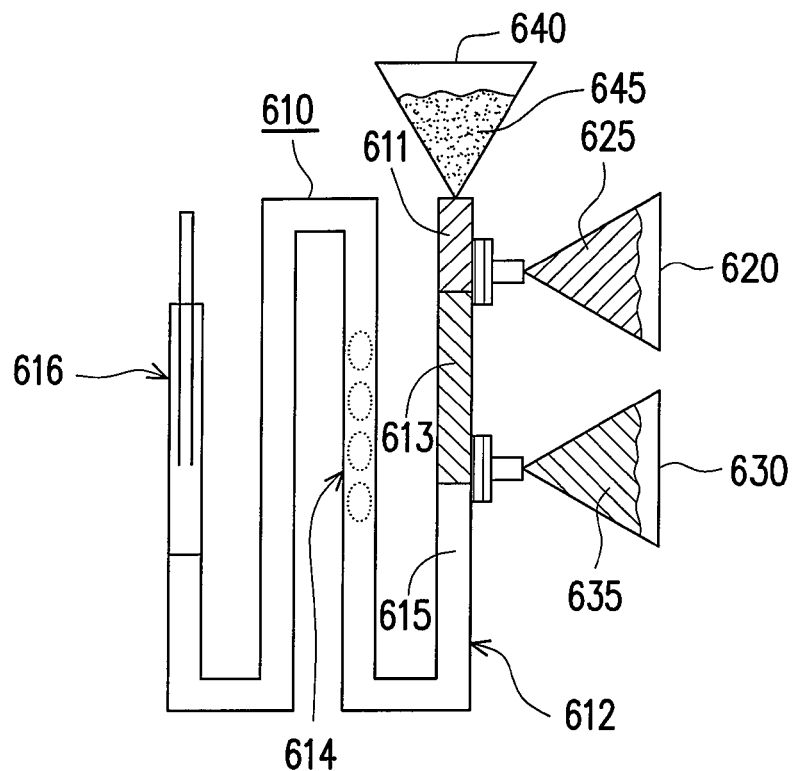
Figure 35D:
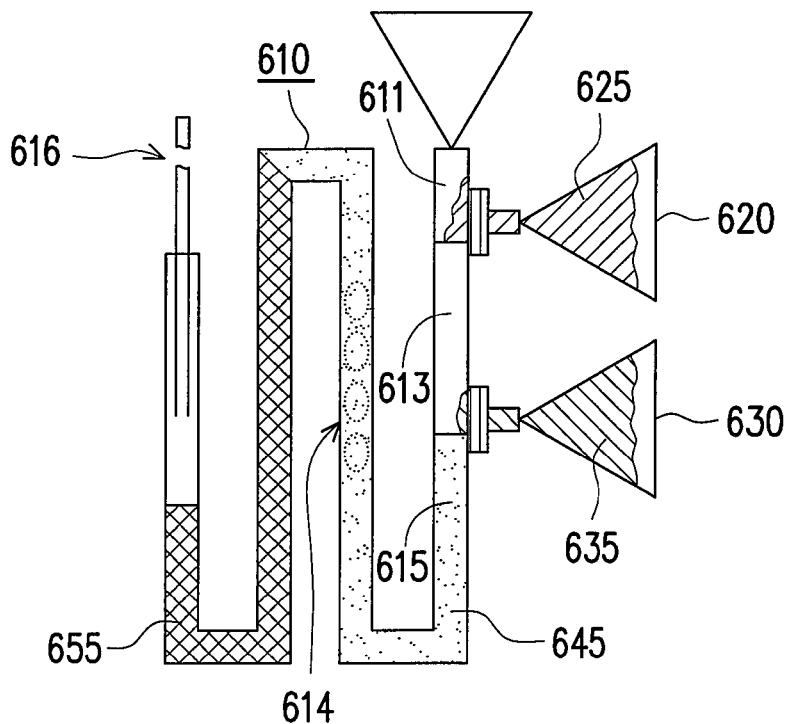

Referring to FIG. 35C, a washing solution 645 is added into the washing well 640. Then, as shown in FIG. 35D, after the broken open valve 616 is activated, an adsorbability is generated to pull the washing solution 645 in the specimen channel 610, the labeled antibody 625 in the area 611, and the blood sample 635 in the area 613, all through the antibody array area 614 so as to perform an antibody assay.

In aforesaid method, the diameter of the specimen channel gradually decreases to increase the capillary force at the channel end, and by using the step design and the time lag valves, the fluid is maintained at a certain volume when flowing into the specific channels. After the sample is infused into the sample well, the labeled antibody is infused into the labeled antibody well, and the washing solution is infused into the washing well, the broken open valve is activated and the fluid is driven by a capillary force to flow through the antibody array area so as to perform the processes of binding, labeling, and washing.

Figure 36A:
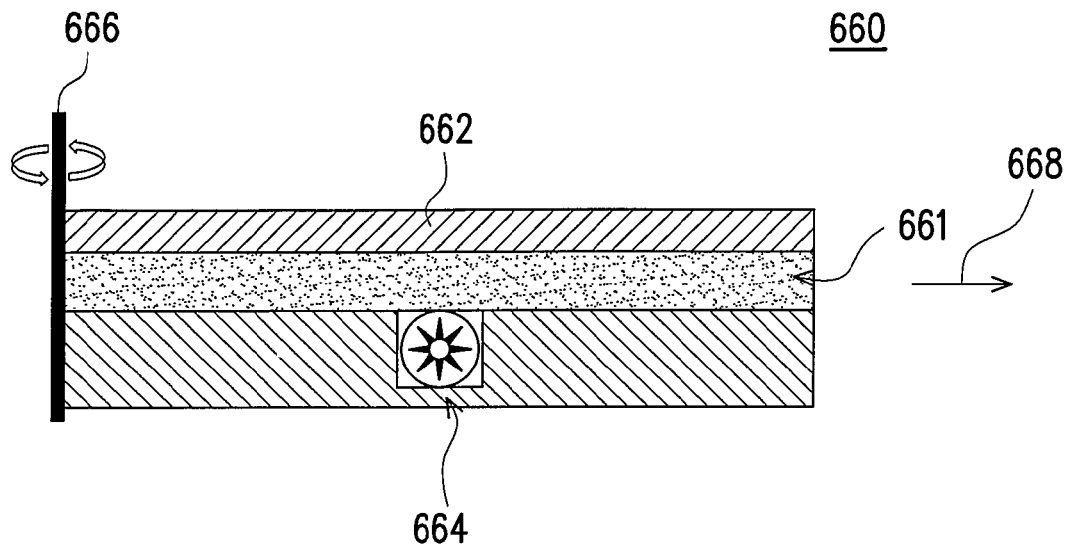
FIGS. 36A and 36B show a blood centrifugal device, which has a time lag valve, in an embodiment of the present invention.
Figure 36B:
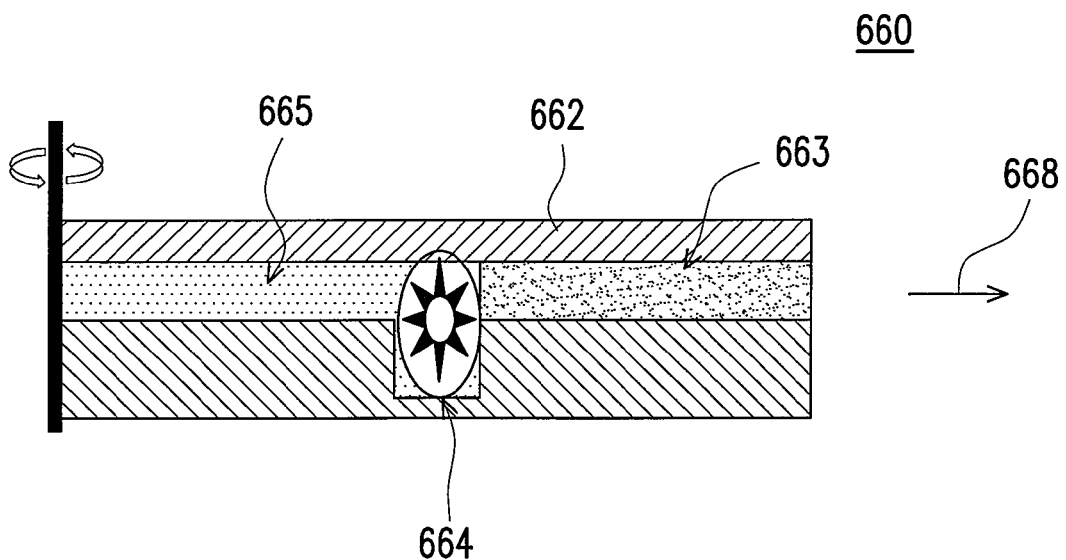

Aforesaid time lag valve is also applicable in, for example, a device for separating blood cells by a centrifugal force, as shown in FIGS. 36A and 36B. In FIGS. 36A and 36B, a whole blood separation device 660, which has a time lag valve, comprises a whole blood separation channel 662. A time lag valve 664 is disposed on a sidewall inside the whole blood separation channel 662. The whole blood separation channel 662 rotates in a centrifugal direction 668 to generate a centrifugal force according to a rotation axis 666. A whole blood sample 661 is infused into the whole blood separation channel 662, and when the whole blood separation channel 662 rotates at a high speed, the blood cells of the whole blood sample 661 gathers toward a centrifugal area to generate a blood cell area 663 and a blood plasma area 665. In the high-speed rotation process, after a water-soluble outer lag layer of the time lag valve 664 dissolves, a superabsorbent polymer absorbs a portion of water and swells to prevent a mixture of the blood cell area 663 and the blood plasma area 665.

Although some examples have been discussed above, other implementations and applications are also within the scope of the following claims. For example, in the vacuum pump 90 of FIGS. 1A and 1B, the container 100 can container a low pressure region instead of a vacuum region. As long as the gas pressure inside the container 100 is lower than the gas pressure outside of the container 100, when the container 100 breaks, the pressure in the region 106 outside of the container 100 will drop, generating a suction force that draws fluids in a direction towards the container 100.

The glass capillaries described above can be replaced by capillaries made of other brittle materials, such as brittle plastic, quartz, and ceramic.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fluidic device, comprising:
    a channel having an expanded section whose diameter is larger than that of the adjacent portions of the expanded section, wherein the fluid device is adapted for allowing a certain amount of a fluid flowing through the channel;
    an absorbent material disposed in the expanded section; and
    a lag material partially coated or wholly coated on the absorbent material, wherein the absorbent material disposed in the expanded section has a volume that does not block the channel before the absorbent material absorbs the fluid, after the lag material dissolves, the absorbent material starts absorbing a portion of the fluid and instantly expands to block the fluid from flowing through.

2. The fluidic device of claim 1, wherein said absorbent material comprises a superabsorbent polymer.

3. The fluidic device of claim 1, wherein said lag material is a water-soluble material.

4. The fluidic device of claim 1, wherein the lag material is a sugar cube or a sugar sheet.

5. A fluid control method adapted for controlling a fluid flowing through a channel, comprising:
    flowing the fluid in the channel, wherein the channel comprises an absorbent material, which is disposed in an expanded section of the channel and instantly expands after absorbing a portion of the fluid, and a lag material, partially coated or wholly coated on the absorbent material in the channel, wherein the absorbent material disposed in the expanded section has a volume that does not block the channel before the absorbent material absorbs the fluid, and after the lag material dissolves, the absorbent material starts absorbing a portion of the fluid and instantly expands to block the fluid from flowing through.

6. The fluid control method of claim 5 wherein the absorbent material comprises a superabsorbent polymer.

7. The fluid control method of claim 5, wherein the lag material is a water-soluble material.

8. The fluid control method of claim 5, wherein the lag material is a sugar cube or a sugar sheet.

9. The fluid control method of claim 5, wherein the lag material is applied on the absorbent material by dip-coating, roll coating or spin coating.

* * * * *